US010506817B2

(12) United States Patent
Fassel et al.

(10) Patent No.: US 10,506,817 B2
(45) Date of Patent: Dec. 17, 2019

(54) FILTRATION SYSTEM

(71) Applicant: Pace International, LLC, Wapato, WA (US)

(72) Inventors: Robert Scott Fassel, Naches, WA (US); Scott Aaron Christie, Yakima, CA (US)

(73) Assignee: PACE INTERNATIONAL, LLC, Wapato, WA (US)

( * ) Notice: Subject to any disclaimer, the term of this patent is extended or adjusted under 35 U.S.C. 154(b) by 26 days.

(21) Appl. No.: 16/106,972

(22) Filed: Aug. 21, 2018

(65) Prior Publication Data

US 2018/0352822 A1 Dec. 13, 2018

Related U.S. Application Data

(63) Continuation-in-part of application No. 15/245,926, filed on Aug. 24, 2016, now Pat. No. 10,258,056, (Continued)

(51) Int. Cl.

| | |
|---|---|
| ***B01D 46/00*** | (2006.01) |
| ***B01D 46/10*** | (2006.01) |
| ***A23B 7/152*** | (2006.01) |
| ***A23B 7/153*** | (2006.01) |

(Continued)

(52) U.S. Cl.

CPC .............. *A23B 7/152* (2013.01); *A01N 25/06* (2013.01); *A01N 43/36* (2013.01); *A01N 43/54* (2013.01); *A01N 43/78* (2013.01); *A23B 7/00* (2013.01); *A23B 7/153* (2013.01); *A23L 3/00* (2013.01); *A23L 3/3445* (2013.01); *B01D 46/00* (2013.01);

(Continued)

(58) Field of Classification Search

CPC ...... B01D 46/00; B01D 46/10; B01D 46/002; B01D 46/0023; A23B 7/152; A23B 7/00; A23B 7/153; A01N 43/54; A01N 43/78; A23L 3/00; A23L 3/3445

USPC ..... 55/385.1, 385.2, 385.4; 95/8, 12, 45, 51, 95/54; 96/4, 11, 397, 417, 421; 426/418, 426/419, 281, 615, 639, 439, 616, 102;

(Continued)

(56) References Cited

U.S. PATENT DOCUMENTS 2,251,617 A * 8/1941 Pirnie ..................... F24F 3/14
34/223
4,226,179 A 10/1980 Sheldon et al.

(Continued)

FOREIGN PATENT DOCUMENTS

EP 2 839 845 2/2015

OTHER PUBLICATIONS

Extended European Search Report dated Feb. 16, 2016 in corresponding EP application No. 13826224.1.

*Primary Examiner* — Minh Chau T Pham

(74) *Attorney, Agent, or Firm* — Wood, Phillips, Katz, Clark & Mortimer

(57) ABSTRACT

A filtration system is arranged to safely vent a storage room into which a fog mixture is introduced. Venting the storage room reduces and/or prevents a substantial increase in the internal pressure of the storage room. To control the pressure differential between the storage room and the ambient air pressure, a venting manifold with an in-line duct fan is used, for example, to exhaust storage room air into the atmosphere. The exhausted storage room air is filtered to reduce the exfiltration of chemicals and/or other contaminants from the environmentally sealed storage room.

4 Claims, 13 Drawing Sheets

Related U.S. Application Data which is a continuation of application No. 15/245, 901, filed on Aug. 24, 2016, now Pat. No. 9,961,913, which is a continuation of application No. 15/223, 414, filed on Jul. 29, 2016, now Pat. No. 9,961,912, which is a continuation of application No. 14/863, 728, filed on Sep. 24, 2015, now Pat. No. 9,433,227, which is a continuation of application No. 13/566, 936, filed on Aug. 3, 2012, now abandoned.

(51) Int. Cl.

| | |
|---|---|
| ***A01N 43/54*** | (2006.01) |
| ***A23L 3/00*** | (2006.01) |
| ***A23L 3/3445*** | (2006.01) |
| ***B01D 46/52*** | (2006.01) |
| ***B01D 50/00*** | (2006.01) |
| ***A23B 7/00*** | (2006.01) |
| ***A01N 25/06*** | (2006.01) |
| ***A01N 43/36*** | (2006.01) |
| ***A01N 43/78*** | (2006.01) |

(52) U.S. Cl.

CPC ......... *B01D 46/002* (2013.01); *B01D 46/521* (2013.01); *B01D 50/00* (2013.01); *A23V 2002/00* (2013.01); *B01D 46/0023* (2013.01); *B01D 46/10* (2013.01); *B01D 2267/30* (2013.01); *B01D 2279/35* (2013.01)

(58) Field of Classification Search

USPC .............. 424/439; 422/3, 4; 99/468; 312/31, 312/31.3, 114, 140

See application file for complete search history.

(56) References Cited

U.S. PATENT DOCUMENTS

| | | | | |
|---|---|---|---|---|
| 4,303,420 | A * | 12/1981 | Howard | B01D 46/22 55/290 |
| 5,009,152 | A | 4/1991 | Morgan | |
| 5,096,474 | A | 3/1992 | Miller et al. | |
| 5,480,538 | A | 1/1996 | McCombs et al. | |
| 5,564,980 | A | 10/1996 | Becker | |
| 5,858,041 | A | 1/1999 | Luetkemeyer | |
| 6,092,430 | A | 7/2000 | Liston et al. | |
| 6,102,977 | A | 8/2000 | Johnson | |
| 6,153,240 | A | 11/2000 | Tottenham et al. | |
| 7,228,793 | B2 | 6/2007 | Ling et al. | |
| 8,177,883 | B2 | 5/2012 | Jorgensen et al. | |
| 8,460,731 | B2 | 6/2013 | Mazin | |
| 9,433,227 | B2 * | 9/2016 | Fassel | A23L 3/00 |
| 9,961,912 | B2 * | 5/2018 | Fassel | A23L 3/00 |
| 9,961,913 | B2 * | 5/2018 | Fassel | A23L 3/00 |
| 2002/0012725 | A1 | 1/2002 | Carlson | |
| 2003/0059509 | A1 | 3/2003 | Grewal | |
| 2003/0072855 | A1 | 4/2003 | Robbs et al. | |
| 2005/0011372 | A1 | 1/2005 | Corrigan et al. | |
| 2005/0288184 | A1 | 12/2005 | Keim et al. | |
| 2008/0274263 | A1 | 11/2008 | Mazin | |
| 2009/0142453 | A1 * | 6/2009 | Lobisser | A23B 7/16 426/102 |
| 2011/0091655 | A1 | 4/2011 | Parling | |
| 2012/0097050 | A1 | 4/2012 | Schaefer et al. | |
| 2013/0209617 | A1 | 8/2013 | Lobisser et al. | |

* cited by examiner

FILTRATION SYSTEM

CROSS-REFERENCE TO RELATED APPLICATIONS

This patent application Ser. No. 16/106,972, filed on Aug. 21, 2018, which is a continuation in part of patent application Ser. No. 15/245,926, filed on Aug. 24, 2016. Patent application Serial No. 15/245,926 is a continuation of Ser. No. 15/245,901, filed on Aug. 24, 2016, now U.S. Pat. No. 9,961,913 B2. Patent application Ser. No. 15/245,901 is a continuation of Ser. No. 15/223,414, filed on Jul. 29, 2016, now U.S. Pat. No. 9,961,912 B2. Patent application Ser. No. 15/223,414 is a continuation of Ser. No. 14/863,728, filed on Sep. 24, 2015, now U.S. Pat. No. 9,433,227 B2. Patent Application Ser. No. 14/863,728 is a continuation of Ser. No. 13/566,936, filed on Aug. 3, 2012, now abandoned. Priority is claimed of the above and all are hereby incorporated by reference in their entireties.

BACKGROUND

Post-harvest chemicals are applied to fruit in environmentally sealed storage rooms. Air and treatment chemicals are applied in the form of a chemical fog mixture. The fog mixture is introduced into the storage room using a device such as an electro-thermofogger gun. The introduction of the externally supplied air in the fog mixture increases the internal pressure of the environmentally sealed storage rooms.

SUMMARY

This summary is provided to introduce a selection of concepts in a simplified form that are further described below in the detailed description. This summary is not intended to identify key features or essential features of the claimed subject matter, nor is it intended as an aid in determining the scope of the claimed subject matter.

A system and method is disclosed herein for safely venting a storage room (such as a commodity storage room) into which a fog mixture is introduced. Venting the storage room reduces and/or prevents a substantial increase in the internal pressure of the storage room. To control the pressure differential between the storage room and the ambient air pressure, a venting manifold with an in-line duct fan is used, for example, to exhaust storage room air into the atmosphere. The exhausted storage room air is filtered to reduce the exfiltration of chemicals and/or other contaminants from the environmentally sealed storage room.

These and other features and advantages will be apparent from a reading of the following detailed description and a review of the associated drawings. It is to be understood that both the foregoing general description and the following detailed description are explanatory only and are not restrictive. Among other things, the various embodiments described herein may be embodied as methods, devices, or a combination thereof. The disclosure herein is, therefore, not to be taken in a limiting sense.

DETAILED DESCRIPTION

Figure 1:
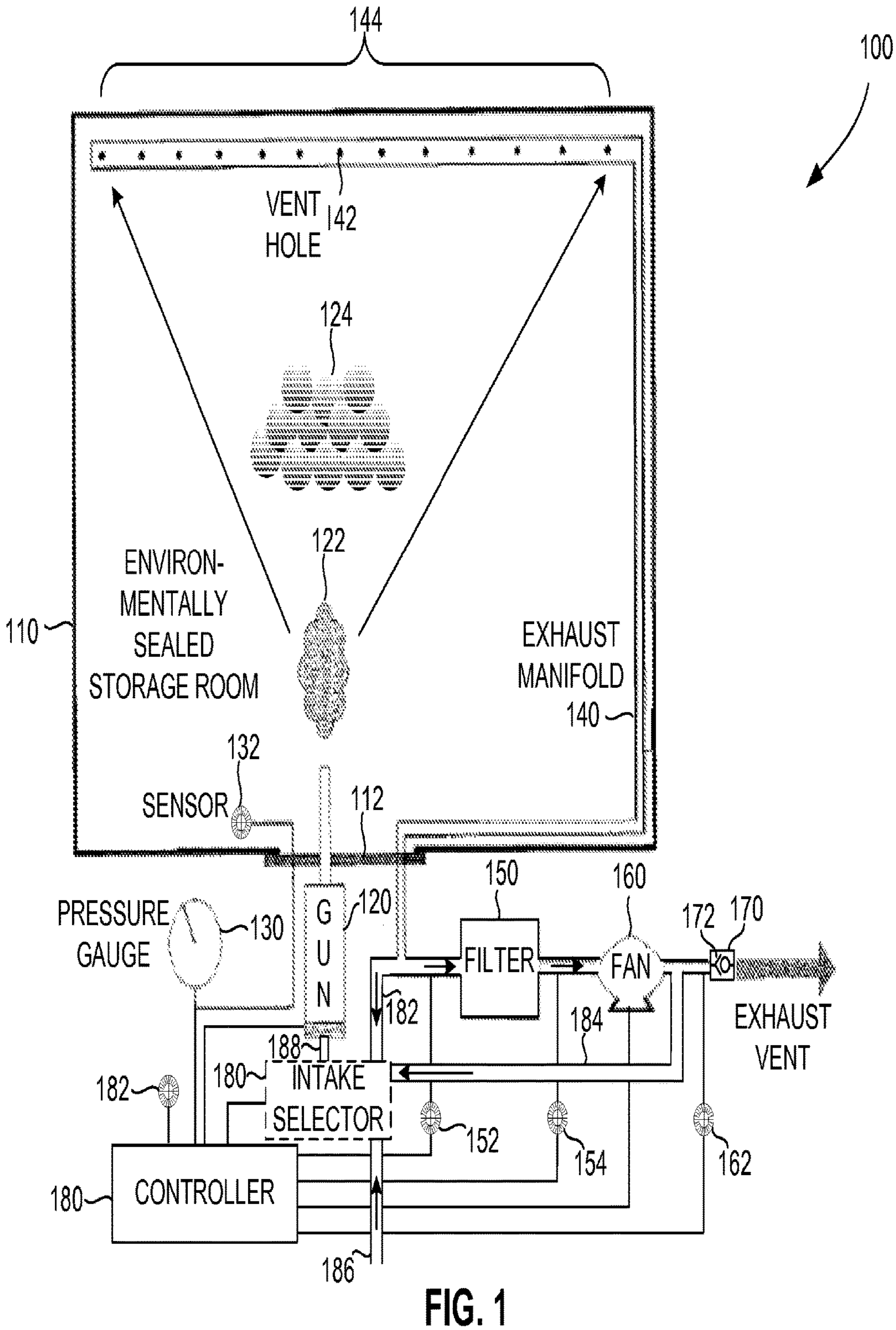
FIG. 1 is a schematic diagram illustrating a thermo-fogging filtration system in accordance with embodiments of the present disclosure.

Various embodiments will be described in detail with reference to the drawings, wherein like reference numerals represent like parts and assemblies throughout the several views. Many details of certain embodiments of the disclosure are set forth in the following description and accompanying figures so as to provide a thorough understanding of the embodiments. Reference to various embodiments does not limit the scope of the claims attached hereto. Additionally, any examples set forth in this specification are not intended to be limiting and merely set forth some of the many possible embodiments for the appended claims.

FIG. 1 is a schematic diagram illustrating a thermo-fogging filtration system in accordance with embodiments of the present disclosure. The thermofogging filtration system 100 includes an environmentally sealed storage room 110 (such as a commodity storage room for storing potatoes) is provided for safely treating items within the environmentally sealed storage room 110. The environmentally sealed storage room 110 is a substantially closed room that is arranged to substantially reduce the introduction of a substantial amount of treatment substances into the surrounding area.

Access to the chamber of the environmentally sealed storage room 110 can be provided using access port 112, which is arranged to allow ingress to and egress from the chamber of the environmentally sealed storage room 110 by, for example, humans and/or items 124 to be treated within the environmentally sealed storage room 110. (In various embodiments, the environmentally sealed storage room 110 is any suitable chamber that need not be large enough to allow a human to enter the environmentally sealed storage room 110.)

An airstream substance infuser is arranged to infuse treatment substances into an airstream to generate air-borne treatment substances. The airstream substance infuser is arranged to introduce the airstream and the air-borne treatment substances into the volume of air of the substantially closed room to generate dispersed air-borne substances. Thermo-fogging gun 120 is an example of an airstream substance infuser that is arranged to infuse treatment substances into an airstream. Thermo-fogging gun 120 is coupled to the environmentally sealed storage room 100 via access port 112, which is normally sealed during times in which items 124 within the environmentally sealed storage room 110 are being treated. During treatment, air-borne substances 122 are introduced into the environmentally sealed storage room 110 by directing the airstream through an exhaust port of the thermo-fogging gun 120. The air-borne substances 122 disperse after being introduced into the environmentally sealed storage room 110 and come in contact with the items 124 that are to be treated.

In an example application, post-harvest chemicals are applied to fruit (or vegetables, including tubers such as potatoes) in sealed storage rooms using a thermo-fogging application method. Air and treatment chemicals in a form such as fog is introduced into a storage room (and/or container) using an electrically driven thermo-fogging gun. The treatment chemicals are dispersed in the storage room using air currents (such as those caused by the thermo-fogging gun itself and/or circulation fans) and (e.g., naturally occurring) diffusion gradients. (The term "fan" means, for example, a device that causes movement of air.) The operation is can be continued (without, for example, interruption) over a period of hours (more or less).

However, the introduction of air-borne substances 122 into the environmentally sealed storage room 110 can increase the air pressure of the environmentally sealed storage room 110. For example, the rise in the air pressure of the environmentally sealed storage room 110 can potentially cause exfiltration of air (and air-borne particles) from the environmentally sealed storage room 110 in accordance with the degree to which the environmentally sealed storage room 110 is, inter alia, airtight. Also, the rise in the air pressure of the environmentally sealed storage room 110 can cause a higher back-pressure to exist relative to the exhaust port of the thermo-fogging gun 120, which can cause a reduction in the efficiency of the thermo-fogging gun as well as a reduction in the efficacy of the air-borne substances 122 treatment process.

An exhaust manifold 140 is provided to prevent a substantial increase in the air pressure of the environmentally sealed storage room 110 (so that, for example, uncontrolled exfiltration is reduced and/or eliminated). In an example embodiment, the exhaust manifold 140 is a plastic tube that is arranged in an area of the environmentally sealed storage room 110 that is at an opposite end of and/or away from the area of the access port 112 such that the air-borne substances traverse a portion of the environmentally sealed storage room 110 that includes items 124 to be treated.

Vent holes 142 are arranged in the exhaust manifold 140 to permit the introduction of air (including air-borne particles) into the exhaust manifold 140. In an example embodiment, the vent holes 142 are three/quarters of an inch in diameter and are spaced on 18 inch centers along a wall of the environmentally sealed storage room 110 that faces the exhaust port of the thermo-fogging gun 120. The air pressure developed in the environmentally sealed storage room 110 by the introduction of the air (that conveys the air-borne substances) into the environmentally sealed storage room 110 facilitates the introduction of air (including air-borne particles) into the exhaust manifold 140. The distributed arrangement of the vent holes 142 along portions of the exhaust manifold 140 (placed along the wall that opposes the exhaust port 112 through which the air-borne substances 122 are introduced into the environmentally sealed storage room 110, for example) promotes a more even dispersion of the air-borne substances throughout the chamber of the environmentally sealed storage room 110.

The exhaust manifold 140 is coupled to a filter 150 that is arranged to capture a portion (including a portion containing substantially all) of the concentration of air-borne particles that have been introduced into the exhaust manifold 140. The filter 150 can be located outside of the environmentally sealed storage room so as to permit easy maintenance and monitoring of the filter 150. (Filter 150 is further described below with reference to FIG. 2.)

To reduce the possibility of exfiltration of air-borne particles from filter 150 (and/or portions of the exhaust manifold 140 that are external to be environmentally sealed storage room 110), and in-line duct fan 160 is coupled to the exhaust of filter 150. In-line duct fan 160 is arranged to provide a negative pressure (e.g., suction) to the exhaustive filter 150. The applied negative pressure can, for example, be used to reduce the pressure of the filter 150 relative to the ambient air pressure (e.g., the air pressure surrounding the environmentally sealed storage room 110).

The reduced internal pressure of filter 150 substantially reduces the potential for the air-borne substances to escape from the filter 150 housing by lessening (and/or even reversing) the pressure gradient between the inside of filter 150 and the outside of filter 150. (As described below, the housing of filter 150 is arranged to be opened to permit maintenance of the filter 150 as well as to permit inspections thereof.) The exhaust of in-line duct fan 160 can be, for example, optionally coupled to another filter and/or installed in series either before or after the filter 150. The exhaust of in-line duct fan 160 can be released as exhaust (through exhaust vent 170) to the ambient air (surrounding environmentally sealed storage room 110). Exhaust vent 170 optionally contains a check valve 172 to, for example, permit portions of the system (as described below) to operate at pressures lower than ambient (e.g., gauge) pressure (which normally reduces the possibility of exfiltration of treatment substances into the ambient air).

In an embodiment, the thermo-fogger gun 120 is arranged to introduce around 30-40 cubic feet per minute (CFM) of an air/chemical mixture into the environmentally sealed storage room 110 in the form of a fog. Controller 180 is arranged to determine ambient pressure (via sensor 182), chamber pressure (via sensor 132), filter intake pressure (via sensor 152), filter exhaust pressure (via sensor 154), and fan exhaust pressure (via sensor 162).

Controller 180 is arranged to control the storage room pressure to a selected value between (for example) −0.15 and +0.15 inches water column (IWC) using a differential pressure reading. The differential pressure reading can be determined by subtracting a reading from sensor 132 with a (nearly contemporaneous) reading from sensor 182. Controller 180 is arranged to control the storage room pressure to a selected value used to control a variable speed in-line duct fan.

Controller 180 can also determine a flow rate through the filter 150 by determining a differential pressure in response to readings from sensor 152 (at the intake of filter 150) and from sensor 154 (at the exhaust of filter 150). An abnormally high pressure differential can indicate a clogged filter (for example) or indicate that service of the filter is to be performed. Pressure sensor 162 can be used in combination other pressure sensors (such as sensor 154) to determine the efficiency of in-line duct fan 160, a blockage of the exhaust manifold upstream or downstream of the sensor 162, and normalization and/or calibration of other sensors.

In various embodiments, controller 180 is optionally arranged to selectively couple one (or more simultaneously) of intakes 182, 184, and 186 to the gun intake 188. When intake 182 is selected, air from the volume of air (including air-borne treatment substances, if any) from environmentally sealed room 110 can be recirculated for injection of additional air-borne treatment substances into the environmentally sealed room. Recirculation via intake 182, for example, extends the life of filter 150, and reduces the possibility that the air-borne substances (not captured by filter 150) might be released to the surrounding area.

When intake 184 is selected, air exhausted from the filter 150 (including air-borne treatment substances, if any) can be recirculated for injection of additional air-borne treatment substances into the environmentally sealed room. Using information from (pressure) sensors 132, 152, 154, 162, and 182, the controller 180 can vary the pressure in selected areas. The pressure of the volumes measured by sensors 152, 154, and 162 can be controlled by selectively controlling the relative speeds of an intake fan of gun 120 and fan 160.

When the flow rate of the fan 160 is increased over the flow rate of the fan of gun 120, the air pressures in between the exhaust of gun 120 and the intake of fan are lowered. Thus, the pressures at points measured by sensors 152, 154, and 162 can be reduced—even to pressures below ambient pressure (which reduces the possibility of exfiltration of the treatment substances to the ambient air). The pressure of the volumes measured by sensors 152, 154, and 162 can be controlled by selectively controlling the relative speed of one or both of fan of gun 120 and fan 160. To help maintain operation of the gun 120 and fan 160 with normal operational parameters, intake 186 (for example) can be selectively opened using a range of settings from a fully open to a fully closed position. (In another exemplary embodiment, check valve 172 can be controlled in a similar fashion).

Recirculation via intake 184 when the flow rate of gun 120 is increased over the flow rate of the fan 160 and check valve 172 is closed (via controller 180, or relative air pressures, for example), reduces the possibility that the air-borne substances (not captured by filter 150) might be released to the surrounding area during a fogging process.

When intake 184 is selected, ambient air is used for by the gun 120 for injection of additional air-borne treatment substances into the environmentally sealed room. The fan 160 is used to motivate air flow in the exhaust manifold, to draw the air-borne substances through filter 150, and to exhaust the filtered air through vent 170 as described above.

Accordingly, the possibility of exfiltration of air-borne substances from the environmentally sealed storage room 110 is reduced, the possibility of exfiltration of air-borne substances from portions of the exhaust manifold 140 and filter 150 is reduced, and the dispersion of the air-borne substances in the environmentally sealed storage room 110 is more evenly distributed in accordance with the distribution of vent holes 142.

Figure 2:
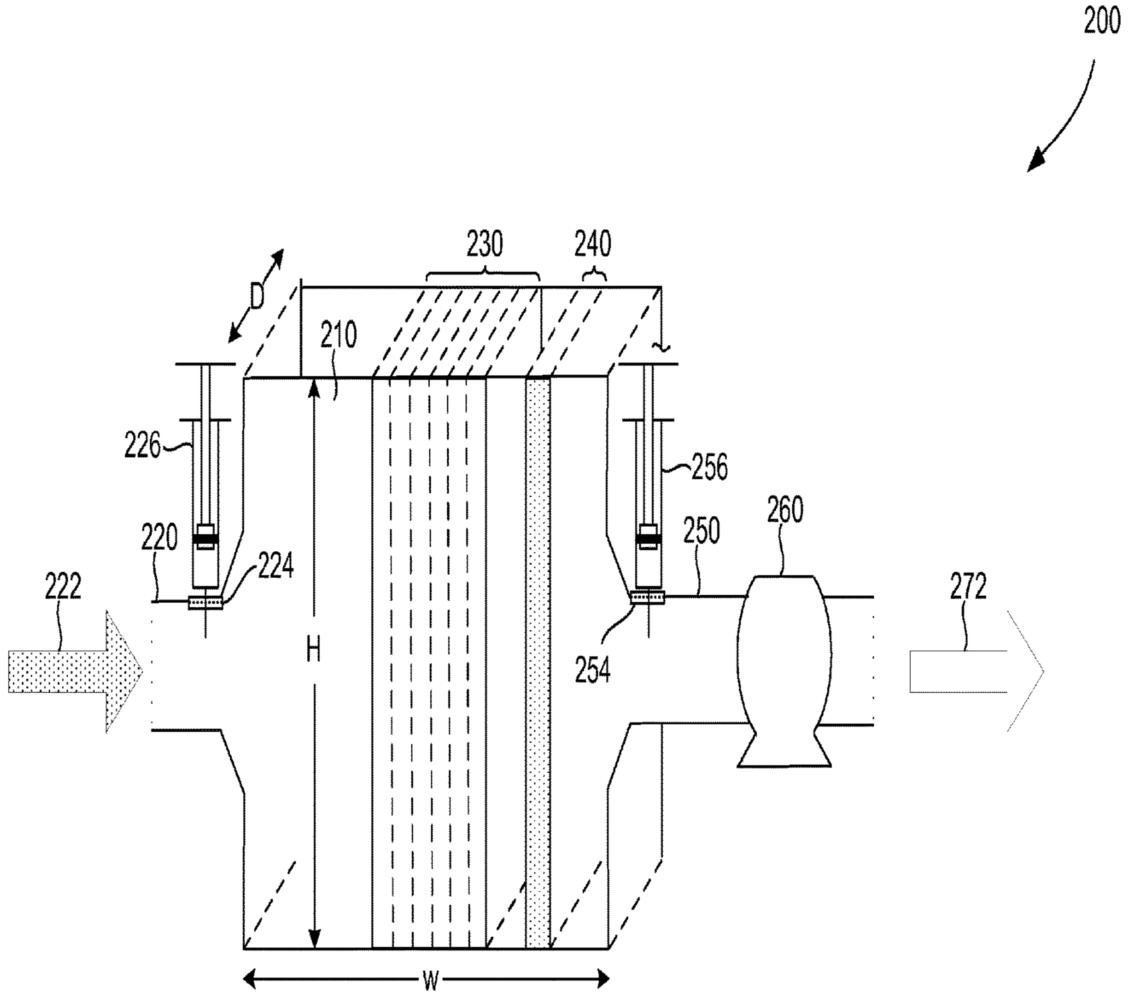
FIG. 2 is an isometric view illustrating a filter system in accordance with embodiments of the present disclosure.

FIG. 2 is an isometric view illustrating a filter system in accordance with embodiments of the present disclosure. The filter system 200 includes a chamber 210 having a width W (e.g., 16 inches), a height H (e.g., 25 inches), and a depth D (e.g., 20 inches). Intake port 220 is arranged to accept an air current 222, which contains air-borne substances that are to be filtered (e.g., removed) by filter system 200. Thus the air current 222 is coupled to chamber 210 via intake port 220, and after being filtered as described below, is exhausted via exhaust port 250. Fan 260 is arranged to motivate the passage of air current 222 through filters of the chamber 210 by evacuating air (in varying degrees as described above) from the chamber 110 and exhausting the evacuated air as air current 272.

Chamber 210 has a first stage filter 230 and a second stage filter 240. The first stage filter 230 in an embodiment is a bank of six "3M" high particle-rated fiber air filters (such as model number 1900 or 2200 and having dimensions of one inch deep by 20 inches wide by 25 inches high) that are arranged in series with respect to the air current flow (such that the air current passes through each fiber air filter in the bank in turn). The first stage filter 230 includes, for example, a series (bank) of pleated fiber filters that are arranged to filter out "visible" air-borne particles. The air-borne particles typically include an active ingredient (AI) used for treating, for example, the items 124 in the environmentally sealed storage room. The first stage filter 230 can include one or more individual filters arranged in a bank.

The second stage filter 240 in an embodiment is a column activated carbon 12×30 mesh (e.g., 1.68 mm×0.595 mm) filter (having outer dimensions of two inches deep by 20 inches wide by 25 inches high). The second stage filter 240 is arranged to capture volatile solvents and odor ("non-visible" air-borne particles) present in the air current 222. The second stage filter 240 can include one or more individual filters arranged in a bank.

The efficiency of the filter system 200 can be made by performing measurements on the quality of the intake air as well as performing measurements on the quality of the exhaust (e.g., filtered) air. In an embodiment, inspection ports 224 and 254 are respectively provided to, for example, to sample the intake air and the exhaust air. The inspection ports 224 and 254 are used to provide a substantially airtight aperture that is arranged to accept a sampling probe. For example the inspection ports 224 and 254 can each include a substantially sealed membrane through which a needle of syringes 226 and 256 is respectively inserted. (The terms "substantially" sealed or airtight are used, for example, to indicate a level at which exfiltration of air-borne substances and/or infiltration of air from the sampling ports would introduce an unacceptable level of error in the measurements.)

Measurements on the quality of the intake air and exhaust air can be performed by measuring by sampling the concentrations of active ingredient (AI) pre-filter (e.g., via inspection port 224) and post-filter (e.g., via inspection port 254). Concentration measurements can be performed by taking aerosol samples at intervals starting, for example, around five to 10 minutes after the beginning of the fogging process (which typically includes introducing treatment substances into the environmentally sealed storage room 110 as described above). In an exemplary embodiment, a first 60 ml-syringe is used to draw a 50 ml sample via inspection port 224 (pre-filter) and a second 60 ml-syringes is used to draw a 50 ml sample via inspection port 254 (post-filter).

A 50 ml sample can be drawn by insert the needle into an inspection port and the plunger slowly drawn back (e.g., pulled up) to the 60 ml mark. After a 10 second delay, the plunger is depressed (e.g., pushed down) to 50 ml mark. The syringe is extracted from the inspection port and used to draw 5 ml of a solvent (such as analytical grade ethyl acetate) into the syringe. The aerosol sample and the solvent are mixed by, for example, removing the needle, capping the syringe outlet, and vigorously shaking the syringe for around 30 seconds. After a 15 second delay (while keeping the syringe vertically oriented with the outlet still capped), the plunger depressed to expel the liquid content (include solvent and solutes) into sampling vials. The level of the active ingredient content of the liquid content in the sampling vials can be determined using a suitable gas chromatography-(GC-) based method.

The efficiency of the filter can be determined by comparing the higher concentration of AI in the pre-filter aerosol sample with the (usually lower) concentration (if any) of AI in a corresponding post-filter aerosol sample. For more accurate determinations, the samples are to be drawn contemporaneously (or substantially contemporaneously) compared to the corresponding outlet sample. The determination can be expressed in accordance with:

$$Cg=100\times CL \quad \text{(I)}$$

where Cg is the concentration of AI in the aerosol (expressed in units of $mg/m^3$) and where CL is the concentration of AI in the liquid solution as determined by the gas chromatography measurement (expressed in units of mg/L or ppm).

Table 1 is a summary of capture efficiencies of various filters tested:

TABLE 1

| Filter Material | AI | AI (mg)/ m^3 min | AI (mg)/ m^3 max | AI (mg)/ m^3 avg | AI reduction min % | AI reduction max % | AI reduction avg % | Wgt gain (g) |
|---|---|---|---|---|---|---|---|---|
| (6) 20" × 25" 3M 2200 air filters + 2" carbon | pyrimethanil | 0 | 0 | 0 | 100 | 100 | 100 | 1074 |
| (6) 20" × 25" 3M 2200 air filters + 2" carbon | pyrimethanil | 0 | 0 | 0 | 100 | 100 | 100 | 1121 |
| (6) 20" × 25" 3M 1900 rated fiber air filter | DPA | 0.1 | 7.7 | 4 | 99.7 | 100 | 99.85 | 266 |
| (6) 20" × 25" 3M 1900 rated fiber air filter | pyrimethanil | 1 | 9 | 4 | 99.3 | 99.8 | 99.6 | 497 |
| (6) 20" × 25" 3M 1900 rated fiber air filter *after 1 room* | pyrimethanil | 3 | 33 | 13 | 90.6 | 99.4 | 97 | |
| (6) 3M 1900 rated fiber air filter ("Merv 13") | pyrimethanil | 55.9 | 191.2 | 95.3 | 94.1 | 98.2 | 96.9 | 1201 |
| (6) 20" × 25" 3M 1900 rated fiber air filter | DPA | 0 | 21.8 | 6.7 | 63.6 | 100 | 93.3 | 1121 |
| (2) low cost fiber filter + (4) 3M 1900 | pyrimethanil | 40 | 80 | 54 | 82.8 | 95.8 | 92.4 | 784 |
| (6) 20" × 25" 3M 1900 rated fiber air filter *after 2nd room* | pyrimethanil | 5 | 276 | 72.7 | 67.8 | 98.8 | 91.5 | 787 |
| (6) 20" × 25" 3M 1900 rated fiber air filter | pyrimethanil | 40 | 60 | 50 | 81 | 98.1 | 89.2 | 1021 |
| (6) re-used 20" × 25" 3M 1900 rated fiber air filter | pyrimethanil | 70 | 160 | 117.5 | 83 | 92.3 | 86.2 | 866 |
| 6" bed Activated coconut carbon-12 × 30 Mesh- Pretreated 10% propylene glycol | pyrimethanil | 30 | 920 | 256 | 57 | 96.2 | 84 | 748 |

TABLE 1-continued

| Filter Material | AI | AI (mg)/ m 3 min | AI (mg)/ m 3 max | AI (mg)/ m 3 avg | AI reduction min % | AI reduction max % | AI reduction avg % | Wgt gain (g) |
|---|---|---|---|---|---|---|---|---|
| (6) 20" × 25" 3M 1900 rated fiber air filter | DPA | 128 | 175 | 143.4 | 67 | 86.5 | 82 | 397 |
| (6) 3M 1900 rated fiber air filter ("Merv 13") washed and dried | pyrimethanil | 90 | 230 | 146 | 58.3 | 92.5 | 81.8 | 901 |
| (6) 3M 1900 rated fiber air filter ("Merv 13") *2nd test* | pyrimethanil | 40 | 130 | 88 | 50 | 91.8 | 80.3 | 1143 |
| 6" bed activated coconut carbon-12 × 30 Mesh- | pyrimethanil | 40 | 580 | 166 | 24.7 | 97 | 79.7 | 934 |
| (2) low cost fiber filter + (4) reused 3M 1900 | pyrimethanil | 60 | 510 | 222 | 45.7 | 88.7 | 78.5 | 658 |
| (6) combo carbon/fiber air filters pretreated with 10% propylene glycol | pyrimethanil | 120 | 1740 | 670 | 48.1 | 74.1 | 58.3 | 284 |
| (6) Low cost fiber filter-600 particle rating | pyrimethanil | 50 | 2600 | 766.7 | −18 | 89.5 | 56.2 | 426 |
| (6) Reusable fiber/sponge filter ("Merv 6") pretreated with 10% propylene glycol | pyrimethanil | 190 | 1840 | 898 | 18.9 | 88.6 | 52.8 | 372 |
| "BPL" coarse 4 × 6 mesh carbon 6" bed | pyrimethanil | 90 | 880 | 370 | 3.3 | 82.5 | 51 | 853 |
| (6) reusable fiber/sponge filter ("Merv 6") | pyrimethanil | 210 | 1641 | 941.7 | 13.1 | 59.2 | 41.78 | 367 |
| (6) combination carbon/fiber air filters | pyrimethanil | 150 | 1730 | 666 | 27.8 | 54.4 | 40.9 | 304 |
| "BPL" coarse 4 × 6 mesh carbon 12" bed | pyrimethanil | 60 | 780 | 285 | 0 | 40.6 | 16 | 839 |

As used herein "DPA" refers to diphenylamine.

As used herein "Pyr" refers to pyrimethanil.

In an embodiment, the present invention is directed to methods for filtration, comprising arranging fruits and/or vegetables in a substantially closed room having a volume of air, introducing a post-harvest chemical, preferably selected from the group consisting of pyrimethanil, diphenylamine, thiabendazole, fludioxonil and a mixture thereof and optionally, additional treatment substances, into an airstream with a thermofogger gun to generate air-borne treatment substances at a rate of up to 80 cubic feet per minute, introducing the airstream and the air-borne treatment substances into the volume of air of the substantially closed room to generate the dispersed air-borne substances, creating with a fan a pressure between −0.25 and 0 inches water column upon a bank of at least six high particle-rated pleated fiber filters, and inducing an exhaust air current that flows from the substantially closed room into an exhaust port of the substantially closed room, wherein the exhaust air current includes the air-borne substances from the exhaust port and the filter bank captures around 95 percent of the air-borne treatment substances.

In an embodiment, the present invention is directed to methods for filtration, comprising arranging fruits and/or vegetables in a substantially closed room having a volume of air, introducing a post-harvest chemical, preferably selected from the group consisting of pyrimethanil, diphenylamine, thiabendazole, fludioxonil and a mixture thereof and optionally, additional treatment substances, into an airstream with a thermofogger gun to generate air-borne treatment substances at a rate of up to 40 cubic feet per minute, introducing the airstream and the air-borne treatment substances into the volume of air of the substantially closed room to generate the dispersed air-borne substances, creating with a fan a pressure between −0.15 and 0 inches water column upon a bank of at least six high particle-rated pleated fiber filters, and inducing an exhaust air current that flows from the substantially closed room into an exhaust port of the substantially closed room, wherein the exhaust air current includes the air-borne substances from the exhaust port and the filter bank captures around 95 percent of the air-borne treatment substances.

Figure 3:
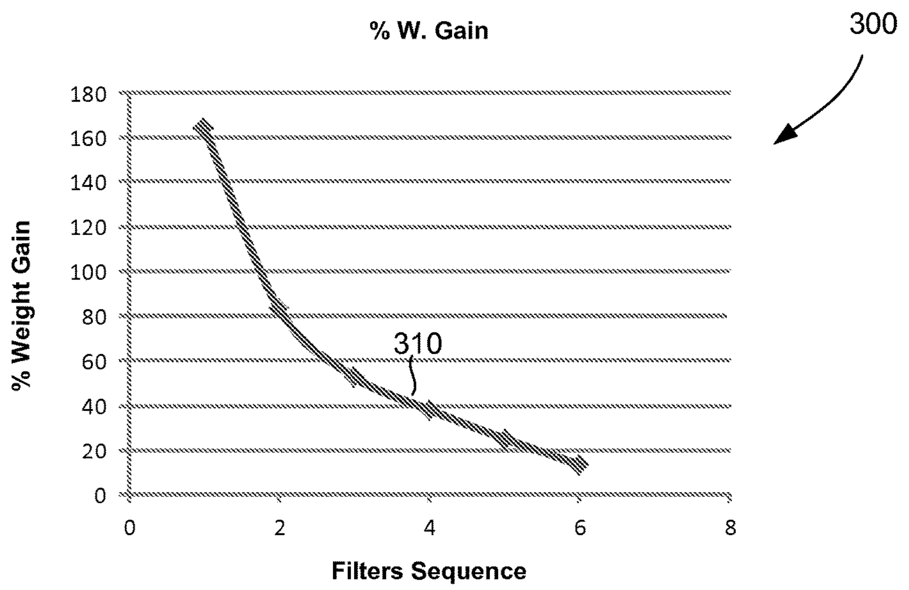
FIG. 3 is a plot diagram that illustrates the efficiency of a "3M" filter bank used in a thermo-fogging filtration system in accordance with embodiments of the present disclosure.

FIG. 3 is a plot diagram that illustrates the efficiency of a "3M" filter bank used in a thermo-fogging filtration system in accordance with embodiments of the present disclosure. Chart 300 includes a plot 310, which illustrate a percentage of weight gain of each "3M" filter of a filter bank (for example) used in an exemplary thermo-fogger filtration system having a total "fog" application time of 45 minutes.

Table 2 is a summary of the weight gain of the "3M" filters tested (due to air-borne substances being captured by each filter, for example):

TABLE 2

| Filters Weight (g) | | | | |
|---|---|---|---|---|
| # | Before | After | Δ m | % W. Gain |
| 1 | 275.98 | 730.5 | 454.52 | 164.7 |
| 2 | 278.19 | 509.29 | 231.1 | 83.1 |
| 3 | 271.49 | 415.21 | 143.72 | 52.9 |
| 4 | 271.21 | 374.49 | 103.28 | 38.1 |
| 5 | 271.16 | 339.58 | 68.42 | 25.2 |
| 6 | 271.12 | 306.63 | 35.51 | 13.1 |
| Total | 1639.15 | 2675.7 | 1036.55 | 63.2 |

Table 3 is a summary of an analysis of the aerosol reduction in a thermo-fogging filtration system using "3M" filters tested:

TABLE 3

| Aerosol Analysis | | | | |
|---|---|---|---|---|
| Sampling Time (min) | Pre-Filter mg Pyr./$M^3$ | After-Filter mg Pyr./$M^3$ | AI Reduction (Times) | % Reduction |
| 5 min | 508.83 | 24.32 | 21 times | 95.2 |
| 25 min | 4891.2 | 452.969 | 11 times | 90.7 |

Figure 4:
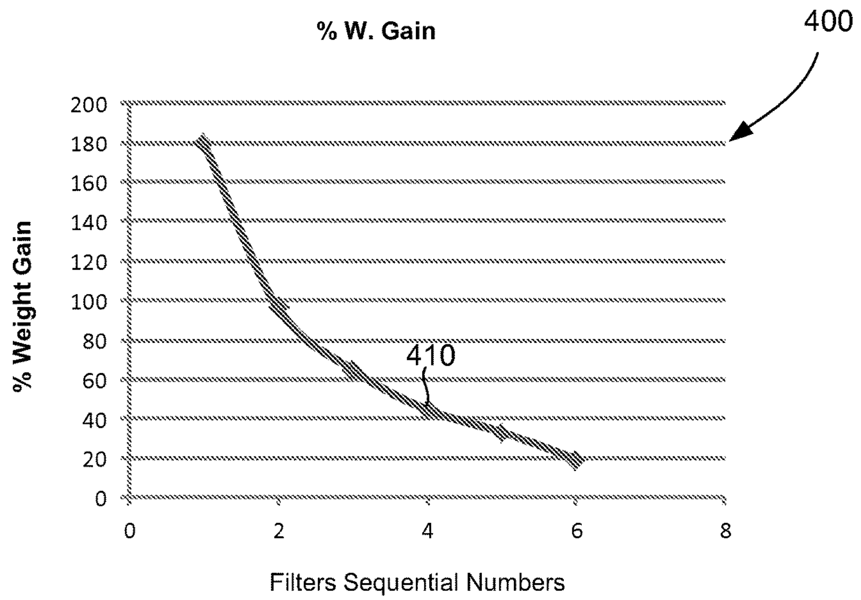
FIG. 4 is a plot diagram that illustrates the efficiency of a "well-sealed 3M" filter bank used in a thermo-fogging filtration system in accordance with embodiments of the present disclosure.

FIG. 4 is a plot diagram that illustrates the efficiency of a "well-sealed 3M" filter bank used in a thermo-fogging filtration system in accordance with embodiments of the present disclosure. Chart 400 includes a plot 410, which illustrate a percentage of weight gain of each "well-sealed 3M" filter of a filter bank (for example) used in an exemplary thermo-fogger filtration system having a total "fog" application time of 135 minutes.

Table 4 is a summary of the weight gain of the "well-sealed 3M" filters tested (due to air-borne substances being captured by each filter, for example):

TABLE 4

| Filters Weight (g) | | | | |
|---|---|---|---|---|
| # | Before | After | Δ m | % W. Gain |
| 1 | 274.53 | 768.15 | 493.62 | 179.8 |
| 2 | 273.94 | 536.91 | 262.97 | 96.0 |
| 3 | 275.63 | 454.37 | 178.74 | 64.8 |
| 4 | 275.68 | 398.83 | 123.15 | 44.7 |
| 5 | 271.67 | 362.18 | 90.51 | 33.3 |
| 6 | 272.15 | 324.3 | 52.15 | 19.2 |
| Total | 1643.6 | 2844.74 | 1201.14 | 73.1 |

Table 5 is a summary of an analysis of the aerosol reduction in a thermo-fogging filtration system using "well-sealed 3M" filters tested:

TABLE 5

| Aerosol Analysis | | | | |
|---|---|---|---|---|
| Sampling Time (min) | Pre-Filter mg Pyr./$M^3$ | After-Filter mg Pyr./$M^3$ | AI Reduction (Times) | % Reduction |
| 5 min | 4311.0 | 113.7 | 37.9 | 97.4 |
| 10 min | 3610.8 | 72.6 | 49.8 | 98.0 |
| 20 min | 4010.0 | 71.4 | 56.1 | 98.2 |
| 35 min | 3244.4 | 191.2 | 17.0 | 94.1 |
| 70 min | 2521.3 | 55.9 | 45.1 | 97.8 |
| 125 min | 1592.1 | 67.2 | 23.7 | 95.8 |

Figure 5:
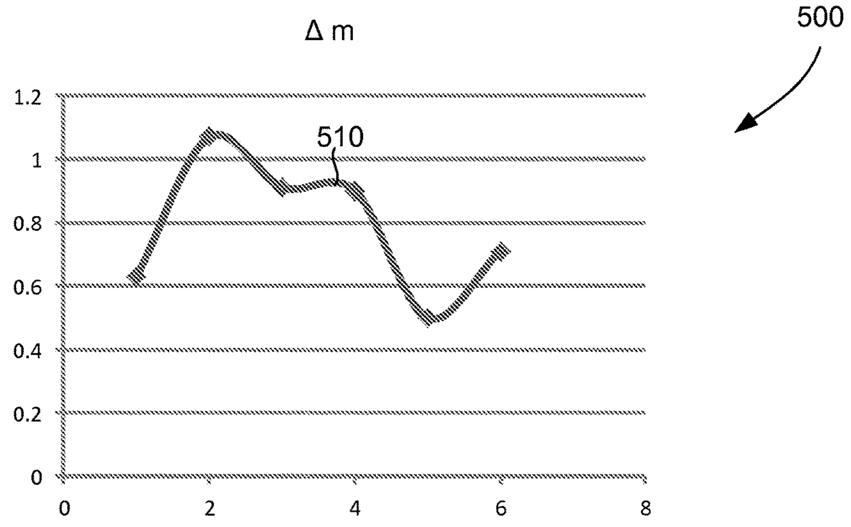
FIG. 5 is a plot diagram that illustrates the efficiency of a "cheap" filter bank used in a thermo-fogging filtration system in accordance with embodiments of the present disclosure.

FIG. 5 is a plot diagram that illustrates the efficiency of a "cheap" filter bank used in a thermo-fogging filtration system in accordance with embodiments of the present disclosure. Chart 500 includes a plot 510, which illustrate a percentage of weight gain of each "cheap" filter of a filter bank (for example) used in an exemplary thermo-fogger filtration system having a total "fog" application time of 15 minutes.

Table 6 is a summary of the weight gain of the "cheap" filters tested (due to air-borne substances being captured by each filter, for example):

TABLE 6

| Filters Weight (g) | | | | |
|---|---|---|---|---|
| # | Before | After | Δ m | % W. Gain |
| 1 | 130.67 | 131.3 | 0.63 | 0.5 |
| 2 | 131.32 | 132.39 | 1.07 | 0.8 |
| 3 | 134.52 | 131.43 | 0.91 | 0.7 |
| 4 | 130.9 | 131.8 | 0.9 | 0.7 |
| 5 | 130.14 | 130.64 | 0.5 | 0.4 |
| 6 | 131.09 | 131.8 | 0.71 | 0.5 |
| Total | 784.64 | 789.36 | 4.72 | 0.6 |

Table 7 is a summary of an analysis of the aerosol reduction in a thermo-fogging filtration system using "cheap" filters tested:

TABLE 7

| Aerosol Analysis | | | | |
|---|---|---|---|---|
| Sampling Time (min) | Pre-Filter mg Pyr./$M^3$ | After-Filter mg Pyr./$M^3$ | AI Reduction (Times) | % Reduction |
| 5 min | 787.7 | 735.4 | 1.1 | 6.6 |

Figure 6:
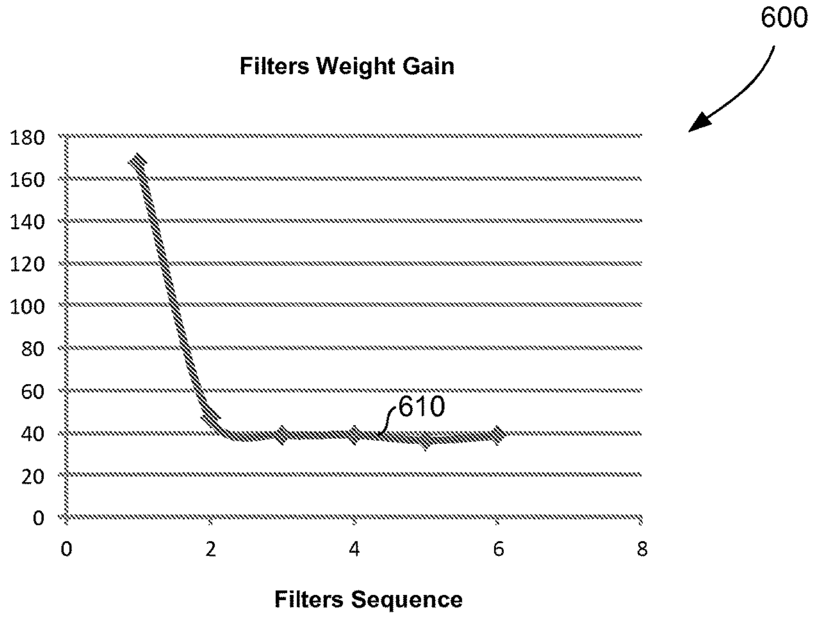
FIG. 6 is a plot diagram that illustrates the efficiency of a "reusable" filter bank used in a thermo-fogging filtration system in accordance with embodiments of the present disclosure.

FIG. 6 is a plot diagram that illustrates the efficiency of a "reusable" filter bank used in a thermo-fogging filtration system in accordance with embodiments of the present disclosure. Chart 600 includes a plot 610, which illustrate a percentage of weight gain of each "reusable" filter of a filter bank (for example) used in an exemplary thermo-fogger filtration system having a total "fog" application time of 165 minutes.

Table 8 is a summary of the weight gain of the "reusable" filters tested (due to air-borne substances being captured by each filter, for example):

TABLE 8

| Filters Weight (g) | | | | |
|---|---|---|---|---|
| # | Before | After | Δ m | % W. Gain |
| 1 | 581.56 | 749.52 | 167.96 | 28.9 |
| 2 | 584.4 | 631.4 | 47 | 8.0 |
| 3 | 584.07 | 623.05 | 38.98 | 6.7 |
| 4 | 579.89 | 618.92 | 39.03 | 6.7 |
| 5 | 580.45 | 616.72 | 36.27 | 6.2 |
| 6 | 583.79 | 622.38 | 38.59 | 6.6 |
| Total | 3494.16 | 3861.99 | 367.83 | 10.5 |

Table 9 is a summary of an analysis of the aerosol reduction in a thermo-fogging filtration system using "reusable" filters tested:

TABLE 9

| Aerosol Analysis | | | | |
|---|---|---|---|---|
| Sampling Time (min) | Pre-Filter mg Pyr./$M^3$ | After-Filter mg Pyr./$M^3$ | AI Reduction (Times) | % Reduction |
| 5 | 1889.9 | 1641.4 | 1.2 | 13.1 |
| 20 | 2989.2 | 1516.9 | 2.0 | 49.3 |
| 50 | 1985.5 | 810.4 | 2.5 | 59.2 |
| 95 | 750 | 530 | 1.4 | 29.3 |
| 155 | 500 | 210 | 2.4 | 58.0 |

Figure 7:
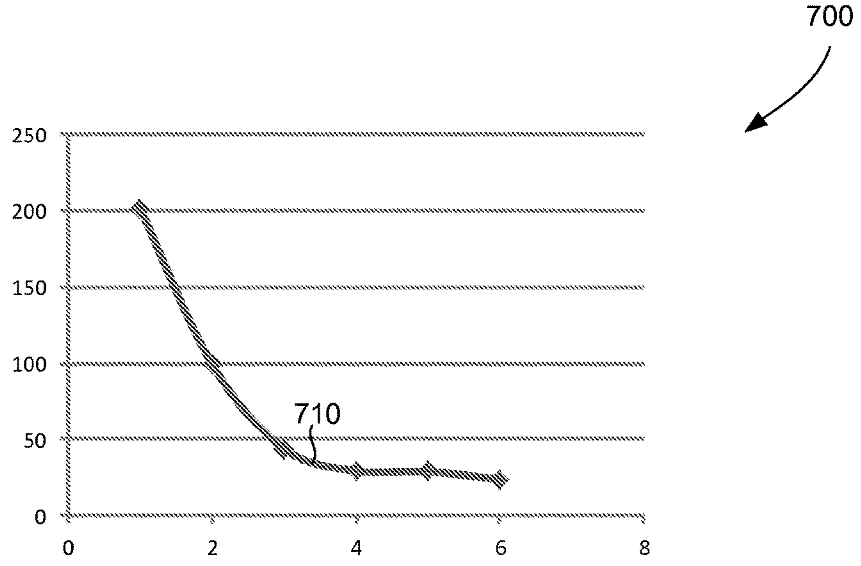
FIG. 7 is a plot diagram that illustrates the efficiency of a "cheap ($2^{nd}$ test)" filter bank used in a thermo-fogging filtration system in accordance with embodiments of the present disclosure.

FIG. 7 is a plot diagram that illustrates the efficiency of a "cheap ($2^{nd}$ test)" filter bank used in a thermo-fogging filtration system in accordance with embodiments of the present disclosure. Chart 700 includes a plot 710, which illustrate a percentage of weight gain of each "cheap ($2^{nd}$ test)" filter of a filter bank (for example) used in an exemplary thermo-fogger filtration system having a total "fog" application time of 152 minutes.

Table 10 is a summary of the weight gain of the "cheap ($2^{nd}$ test)" filters tested (due to air-borne substances being captured by each filter, for example):

TABLE 10

| Filters Weight (g) | | | | |
|---|---|---|---|---|
| # | Before | After | Δ m | % W. Gain |
| 1 | 126.59 | 328.27 | 201.68 | 159.3 |
| 2 | 125.07 | 224.5 | 99.43 | 79.5 |
| 3 | 126.65 | 170.16 | 43.51 | 34.4 |
| 4 | 125.06 | 154.4 | 29.34 | 23.5 |
| 5 | 129.27 | 158.1 | 28.83 | 22.3 |
| 6 | 122.5 | 145.96 | 23.46 | 19.2 |
| Total | 755.14 | 1181.39 | 426.25 | 56.4 |

Table 11 is a summary of an analysis of the aerosol reduction in a thermo-fogging filtration system using "cheap (2nd test)" filters tested:

TABLE 11

| Aerosol Analysis | | | | |
|---|---|---|---|---|
| Sampling Time (min) | Pre-Filter mg Pyr./M$^3$ | After-Filter mg Pyr./M$^3$ | AI Reduction (Times) | % Reduction |
| 7 | 2784 | 2600 | 1.1 | 6.6 |
| 27 | 1332 | 1570 | 0.8 | −17.9 |
| 47 | 1715 | 180 | 9.5 | 89.5 |
| 72 | 1203 | 130 | 9.3 | 89.2 |
| 112 | 491 | 70 | 7.0 | 85.7 |
| 142 | 315 | 50 | 6.3 | 84.1 |

Figure 8:
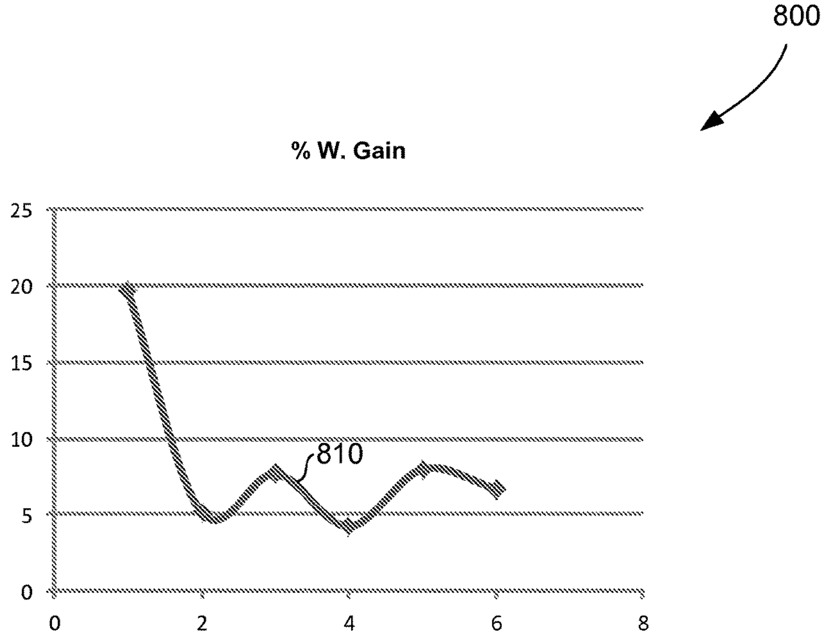
FIG. 8 is a plot diagram that illustrates the efficiency of a "reusable filters pretreated with propylene glycol" (PG) filter bank used in a thermo-fogging filtration system in accordance with embodiments of the present disclosure.

FIG. 8 is a plot diagram that illustrates the efficiency of a "reusable filters pretreated with propylene glycol" (PG) filter bank used in a thermo-fogging filtration system in accordance with embodiments of the present disclosure. Chart 800 includes a plot 810, which illustrate a percentage of weight gain of each "reusable filters pretreated with PG" filter of a filter bank (for example) used in an exemplary thermo-fogger filtration system having a total "fog" application time of 165 minutes.

Table 12 is a summary of the weight gain of the "reusable filters pretreated with PG" filters tested (due to air-borne substances being captured by each filter, for example):

TABLE 12

| Filters Weight (g) | | | | | |
|---|---|---|---|---|---|
| # | Before | After | Δ m | PG on fltr | % W. Gain |
| 1 | 643.65 | 800.4 | 156.75 | 48.91 | 19.6 |
| 2 | 642.81 | 677.4 | 34.59 | 54.78 | 5.1 |
| 3 | 619.7 | 671.75 | 52.05 | 34.1 | 7.7 |
| 4 | 627.5 | 655.07 | 27.57 | 94.7 | 4.2 |
| 5 | 629.3 | 683.96 | 54.66 | 45.7 | 8.0 |
| 6 | 643.95 | 690.3 | 46.35 | 58.22 | 6.7 |
| Total | 3806.91 | 4178.88 | 371.97 | 336.41 | 8.9 |

Table 13 is a summary of an analysis of the aerosol reduction in a thermo-fogging filtration system using "reusable filters pretreated with PG" filters tested:

TABLE 13

| Aerosol Analysis | | | | |
|---|---|---|---|---|
| Sampling Time (min) | Pre-Filter mg Pyr./M$^3$ | After-Filter mg Pyr./M$^3$ | AI Reduction (Times) | % Reduction |
| 5 | 1220 | 990 | 1.2 | 18.9 |
| 25 | 2550 | 1840 | 1.4 | 27.8 |
| 45 | 2330 | 970 | 2.4 | 58.4 |
| 85 | 1690 | 50D | 3.4 | 70.4 |
| 145 | 1660 | 19D | 8.7 | 88.6 |

The efficiency of an "activated carbon six inches" filter used in a thermo-fogging filtration system in accordance with embodiments of the present disclosure is now discussed. Tables 14 and 15 illustrate measurements taken when using an "activated carbon six inches" filter (for example) used in an exemplary thermo-fogger filtration system having a total "fog" application time of 125 minutes.

Table 14 is a summary of the weight gain of the "activated carbon six inches" filters tested (due to air-borne substances being captured by each filter, for example):

TABLE 14

| Filters Weight (g) | | | | |
|---|---|---|---|---|
| # | Before | After | Δ m | % W. Gain |
| 1 | 20411.7 | 21346.1 | 934.4 | 4.6 |
| Total | 20411.7 | 21346.1 | 934.4 | 4.6 |

Table 15 is a summary of an analysis of the aerosol reduction in a thermo-fogging filtration system using "activated carbon six inches" filters tested:

TABLE 15

| Aerosol Analysis | | | | |
|---|---|---|---|---|
| Sampling Time (min) | Pre-Filter mg Pyr./M$^3$ | After-Filter mg Pyr./M$^3$ | AI Reduction (Times) | % Reduction |
| 5 | 770 | 580 | 1.3 | 24.7 |
| 35 | 3030 | 90 | 33.7 | 97.0 |
| 65 | 1940 | 70 | 27.7 | 96.4 |
| 95 | 770 | 40 | 19.3 | 94.8 |
| 125 | 350 | 50 | 7.0 | 85.7 |

The efficiency of an "activated carbon six inches (pretreated)" filter used in a thermo-fogging filtration system in accordance with embodiments of the present disclosure is now discussed. The activated carbon six inches filter was pretreated with a 10% solution of PG. Tables 16 and 17 illustrate measurements taken when using an "activated carbon six inches (pretreated)" filter (for example) used in an exemplary thermo-fogger filtration system having a total "fog" application time of 125 minutes.

Table 16 is a summary of the weight gain of the "activated carbon six inches (pretreated)" filters tested (due to air-borne substances being captured by each filter, for example):

TABLE 16

| Filters Weight (g) | | | | |
|---|---|---|---|---|
| # | Before | After | Δ m | % W. Gain |
| 1 | 23586.8 | 24335.2 | 748.4 | 3.2 |
| Total | 23586.B | 24335.2 | 748.4 | 3.2 |

Table 17 is a summary of an analysis of the aerosol reduction in a thermo-fogging filtration system using "activated carbon six inches (pretreated)" filters tested:

TABLE 17

| Aerosol Analysis | | | | |
|---|---|---|---|---|
| Sampling Time (min) | Pre-Filter mg Pyr./$M^3$ | After-Filter mg Pyr./$M^3$ | AI Reduction (Times) | % Reduction |
| 5 | 2140 | 920 | 2.3 | 57.0 |
| 35 | 1830 | 230 | 8.0 | 87.4 |
| 65 | 1310 | 50 | 26.2 | 96.2 |
| 95 | 540 | 50 | 10.8 | 90.7 |
| 125 | 260 | 30 | 8.7 | 88.5 |

Figure 9:
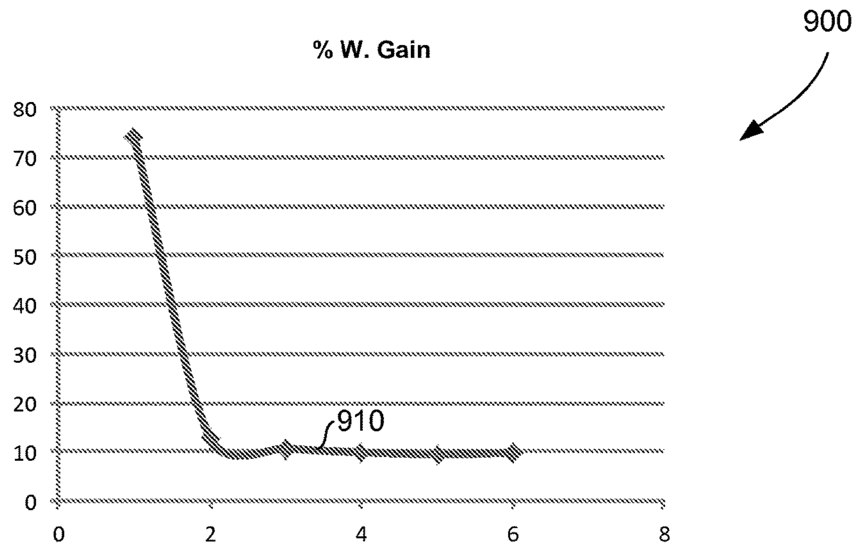
FIG. 9 is a plot diagram that illustrates the efficiency of a "carbon/fiber filter (untreated)" filter bank used in a thermo-fogging filtration system in accordance with embodiments of the present disclosure.

FIG. 9 is a plot diagram that illustrates the efficiency of a "carbon/fiber filter (untreated)" filter bank used in a thermo-fogging filtration system in accordance with embodiments of the present disclosure. Chart 900 includes a plot 910, which illustrate a percentage of weight gain of each "carbon/fiber filter (untreated)" filter of a filter bank (for example) used in an exemplary thermo-fogger filtration system having a total "fog" application time of 125 minutes.

Table 18 is a summary of the weight gain of the "carbon/fiber filter (untreated)" filters tested (due to air-borne substances being captured by each filter, for example):

TABLE 18

| Filters Weight (g) | | | | |
|---|---|---|---|---|
| # | Before | After | Δ m | % W. Gain |
| 1 | 239.73 | 417.67 | 177.94 | 74.2 |
| 2 | 240.6 | 271.39 | 30.79 | 12.8 |
| 3 | 239.56 | 265.13 | 25.57 | 10.7 |
| 4 | 244.23 | 268.52 | 24.29 | 9.9 |
| 5 | 238.55 | 260.86 | 22.31 | 9.4 |
| 6 | 237.39 | 260.61 | 23.22 | 9.8 |
| Total | 1440.06 | 1744.18 | 304.12 | 21.1 |

Table 19 is a summary of an analysis of the aerosol reduction in a thermo-fogging filtration system using "carbon/fiber filter (untreated)" filters tested:

TABLE 19

| Aerosol Analysis | | | | |
|---|---|---|---|---|
| Sampling Time (min) | Pre-Filter mg Pyr./$M^3$ | After-Filter mg Pyr./$M^3$ | AI Reduction (Times) | % Reduction |
| 5 | 180 | 130 | 1.4 | 27.8 |
| 35 | 3090 | 1730 | 1.8 | 44.0 |
| 65 | 2060 | 940 | 2.2 | 54.4 |
| 95 | 640 | 380 | 0.6 | 40.6 |
| 125 | 240 | 150 | 1.6 | 37.5 |

Figure 10:
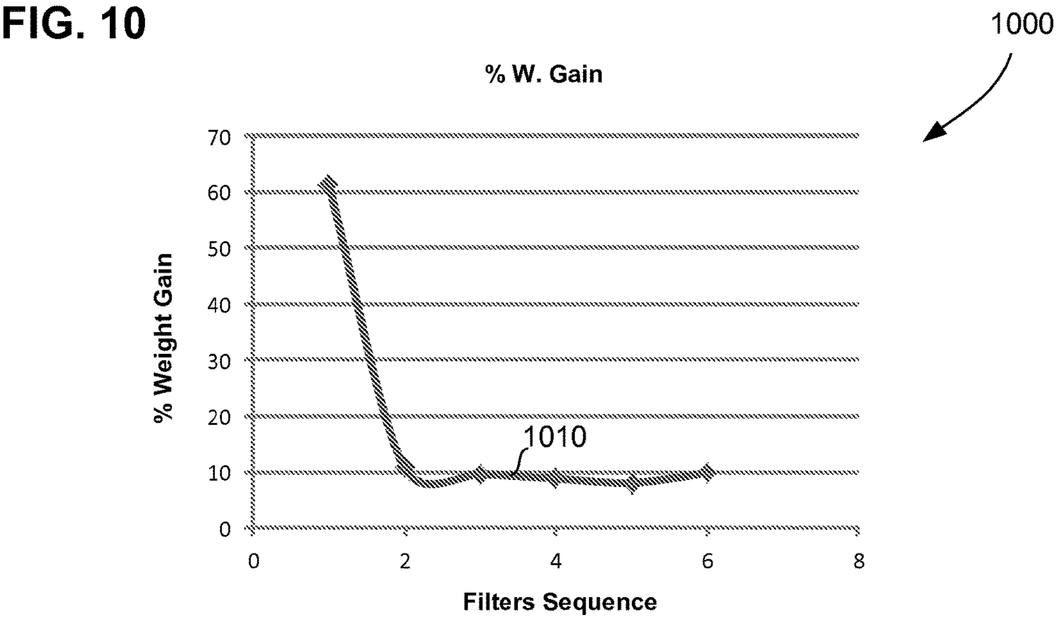
FIG. 10 is a plot diagram that illustrates the efficiency of a "carbon/fiber filter (10% PG)" filter bank used in a thermo-fogging filtration system in accordance with embodiments of the present disclosure.

FIG. 10 is a plot diagram that illustrates the efficiency of a "carbon/fiber filter (10% PG)" filter bank used in a thermo-fogging filtration system in accordance with embodiments of the present disclosure. Chart 1000 includes a plot 1010, which illustrate a percentage of weight gain of each "carbon/fiber filter (10% PG)" filter of a filter bank (for example) used in an exemplary thermo-fogger filtration system having a total "fog" application time of 125 minutes.

Table 20 is a summary of the weight gain of the "carbon/fiber filter (10% PG)" filters tested (due to air-borne substances being captured by each filter, for example):

TABLE 20

| Filters Weight (g) | | | | |
|---|---|---|---|---|
| # | Before | After | Δ m | % W. Gain |
| 1 | 261.2 | 421.31 | 160.11 | 61.3 |
| 2 | 263.74 | 291.9 | 28.16 | 10.7 |
| 3 | 264.44 | 289.9 | 25.46 | 9.6 |
| 4 | 265.11 | 288.31 | 23.2 | 8.8 |
| 5 | 264.13 | 285.17 | 21.04 | 8.0 |
| 6 | 269.35 | 295.75 | 26.4 | 9.8 |
| Total | 1587.97 | 1872.34 | 284.37 | 17.9 |

Table 21 is a summary of an analysis of the aerosol reduction in a thermo-fogging filtration system using "carbon/fiber filter (10% PG)" filters tested:

TABLE 21

| Aerosol Analysis | | | | |
|---|---|---|---|---|
| Sampling Time (min) | Pre-Filter mg Pyr./$M^3$ | After-Filter mg Pyr./$M^3$ | AI Reduction (Times) | % Reduction |
| 5 | 580 | 150 | 3.9 | 74.1 |
| 35 | 3490 | 1740 | 2.0 | 50.1 |
| 65 | 2060 | 940 | 2.2 | 54.4 |
| 95 | 770 | 400 | 1.9 | 48.1 |
| 125 | 340 | 120 | 2.8 | 64.7 |

Figure 11:
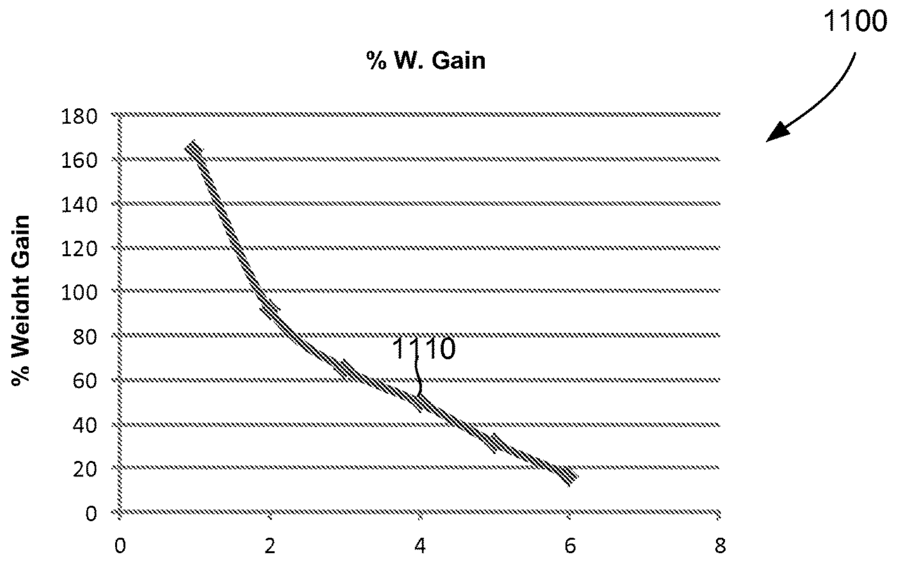
FIG. 11 is a plot diagram that illustrates the efficiency of a "3M filter (Second Test)" filter bank used in a thermo-fogging filtration system in accordance with embodiments of the present disclosure.

FIG. 11 is a plot diagram that illustrates the efficiency of a "3M filter (Second Test)" filter bank used in a thermo-fogging filtration system in accordance with embodiments of the present disclosure. Chart 1100 includes a plot 1110, which illustrate a percentage of weight gain of each "3M filter (Second Test)" filter of a filter bank (for example) used in an exemplary thermo-fogger filtration system having a total "fog" application time of 140 minutes.

Table 22 is a summary of the weight gain of the "3M filter (Second Test)" filters tested (due to air-borne substances being captured by each filter, for example):

TABLE 22

| Filters Weight (g) | | | | |
|---|---|---|---|---|
| # | Before | After | Δ m | % W. Gain |
| 1 | 273.13 | 722.62 | 449.49 | 164.6 |
| 2 | 271.97 | 522.04 | 250.07 | 91.9 |
| 3 | 274.07 | 452.04 | 177.97 | 64.9 |
| 4 | 2737 | 409.77 | 136.07 | 49.7 |
| 5 | 271.01 | 355.75 | 84.74 | 31.3 |
| 6 | 271.08 | 315.8 | 44.72 | 16.5 |
| Total | 1634.96 | 2778.02 | 1143.06 | 69.9 |

Table 23 is a summary of an analysis of the aerosol reduction in a thermo-fogging filtration system using "3M filter (Second Test)" filters tested:

TABLE 23

| Aerosol Analysis | | | | |
|---|---|---|---|---|
| Sampling Time (min) | Pre-Filter mg Pyr./$M^3$ | After-Filter mg Pyr./$M^3$ | AI Reduction (Times) | % Reduction |
| 5 | 970 | 80 | 12.1 | 91.8 |
| 35 | 1530 | 130 | 11.8 | 91.5 |
| 65 | 1120 | 90 | 12.4 | 92.0 |
| 95 | 340 | 110 | 3.1 | 67.6 |
| 125 | 160 | 80 | 2.0 | 50.0 |
| 135 | 360 | 40 | 9.0 | 88.9 |

Figure 12:
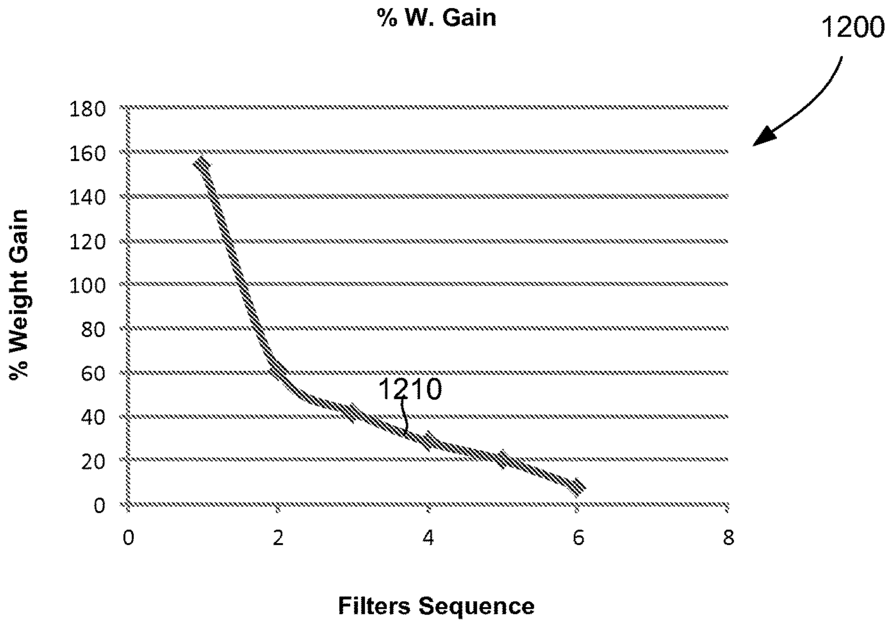
FIG. 12 is a plot diagram that illustrates the efficiency of a "3M filter (washed and dried)" filter bank used in a thermo-fogging filtration system in accordance with embodiments of the present disclosure.

FIG. 12 is a plot diagram that illustrates the efficiency of a "3M filter (washed and dried)" filter bank used in a thermo-fogging filtration system in accordance with embodiments of the present disclosure. Chart 1100 includes a plot 1110, which illustrate a percentage of weight gain of each "3M filter (washed and dried)" filter of a filter bank (for example) used in an exemplary thermo-fogger filtration system having a total "fog" application time of 125 minutes.

Table 24 is a summary of the weight gain of the "3M filter (washed and dried)" filters tested (due to air-borne substances being captured by each filter, for example):

TABLE 24

| Filters Weight (g) | | | | |
|---|---|---|---|---|
| # | Before | After | Δ m | % W. Gain |
| 1 | 276.45 | 701.69 | 425.24 | 153.8 |
| 2 | 290.66 | 466.66 | 176 | 60.6 |
| 3 | 295 | 417.88 | 122.86 | 41.7 |
| 4 | 299.72 | 384.53 | 84.81 | 28.3 |
| 5 | 313.3 | 375.82 | 62.52 | 20.0 |
| 6 | 375.2 | 404.6 | 29.4 | 7.8 |
| Total | 1850.33 | 2751.18 | 900.85 | 48.7 |

Table 25 is a summary of an analysis of the aerosol reduction in a thermo-fogging filtration system using "3M filter (washed and dried)" filters tested:

TABLE 25

| Aerosol Analysis | | | | |
|---|---|---|---|---|
| Sampling Time (min) | Pre-Filter mg Pyr./$M^3$ | After-Filter mg Pyr./$M^3$ | AI Reduction (Times) | % Reduction |
| 5 | 520 | 90 | 5.8 | 82.7 |
| 35 | 2200 | 230 | 9.6 | 89.5 |
| 65 | 1870 | 140 | 13.4 | 92.5 |
| 95 | 860 | 120 | 7.2 | 86.0 |
| 125 | 360 | 150 | 2.4 | 58.3 |

Figure 13:
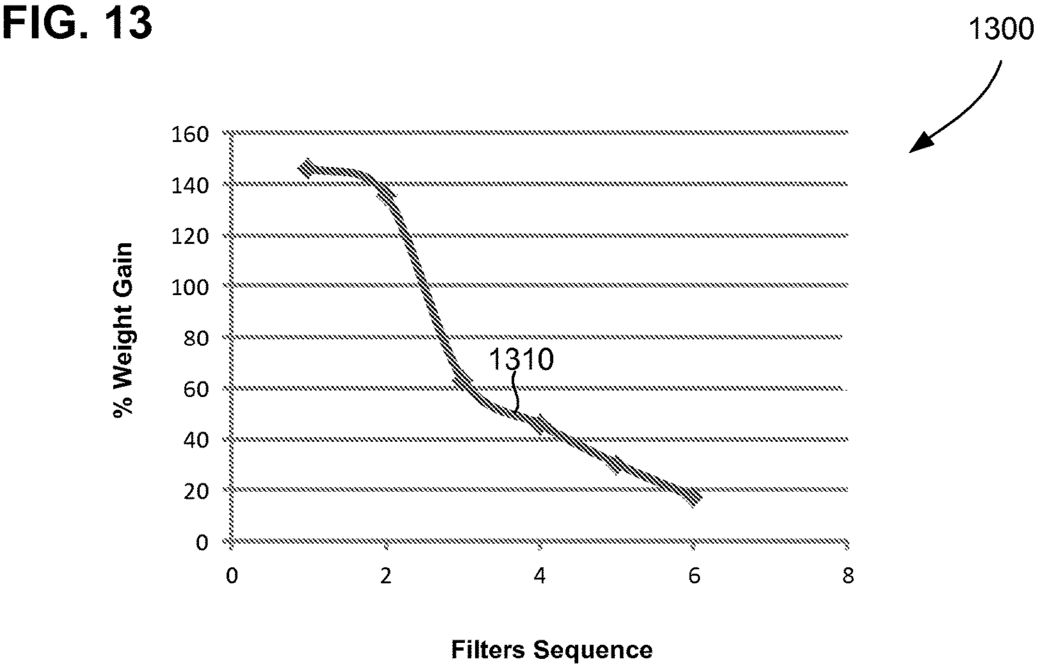
FIG. 13 is a plot diagram that illustrates the efficiency of a "two cheap and four 3M filters" filter bank used in a thermo-fogging filtration system in accordance with embodiments of the present disclosure.

FIG. 13 is a plot diagram that illustrates the efficiency of a "two cheap and four 3M filters" filter bank used in a thermo-fogging filtration system in accordance with embodiments of the present disclosure. Chart 1300 includes a plot 1310, which illustrate a percentage of weight gain of each "two cheap and four 3M filters" filter of a filter bank (for example) used in an exemplary thermo-fogger filtration system having a total "fog" application time of 125 minutes.

Table 26 is a summary of the weight gain of the "two cheap and four 3M filters" filters tested (due to air-borne substances being captured by each filter, for example):

TABLE 26

| Filters Weight (g) | | | | |
|---|---|---|---|---|
| # | Before | After | Δ m | % W. Gain |
| 1 | 126.42 | 311.21 | 184.79 | 146.2 |
| 2 | 123.35 | 290.91 | 167.56 | 135.8 |
| 3 | 274.17 | 447.07 | 172.9 | 63.1 |
| 4 | 275.67 | 402.02 | 126.35 | 45.8 |
| 5 | 276.46 | 360.24 | 83.78 | 30.3 |
| 6 | 276.33 | 324.74 | 48.41 | 17.5 |
| Total | 1352.4 | 2136.19 | 783.79 | 58.0 |

Table 27 is a summary of an analysis of the aerosol reduction in a thermo-fogging filtration system using "two cheap and four 3M filters" filters tested:

TABLE 27

| Aerosol Analysis | | | | |
|---|---|---|---|---|
| Sampling Time (min) | Pre-Filter mg Pyr./$M^3$ | After-Filter mg Pyr./$M^3$ | AI Reduction (Times) | % Reduction |
| 5 | 1790 | 80 | 22.4 | 95.5 |
| 35 | 1330 | 60 | 22.2 | 95.5 |
| 65 | 950 | 40 | 23.8 | 95.8 |
| 95 | 290 | 50 | 5.8 | 82.8 |
| 125 | 540 | 40 | 13.5 | 92.6 |

Figure 14:
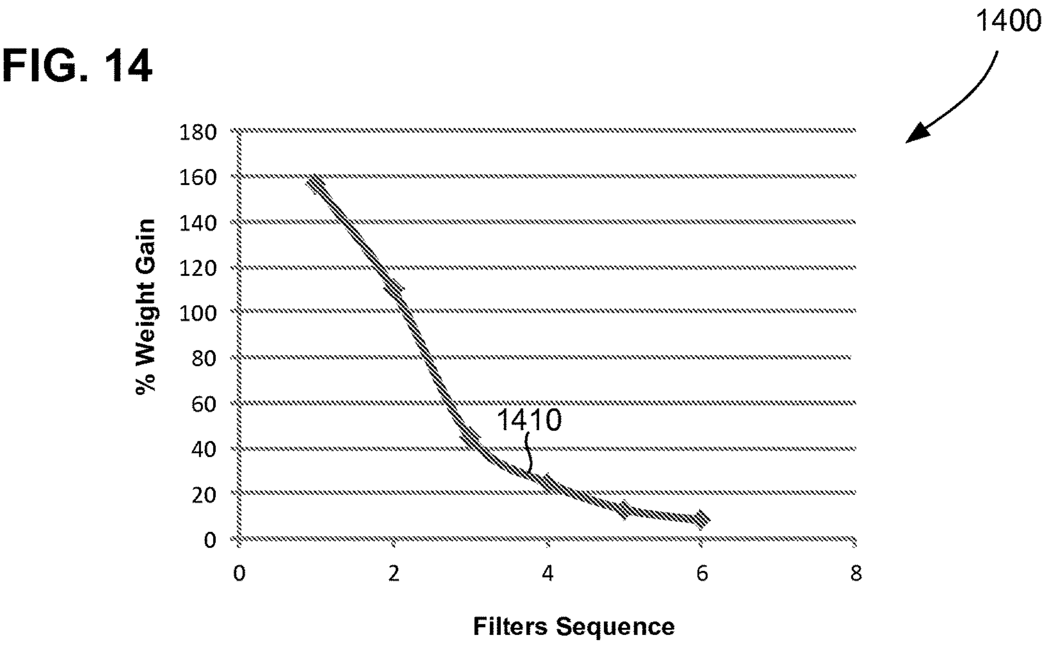
FIG. 14 is a plot diagram that illustrates the efficiency of a "two cheap and four 3M filters (reused)" filter bank used in a thermo-fogging filtration system in accordance with embodiments of the present disclosure.

FIG. 14 is a plot diagram that illustrates the efficiency of a "two cheap and four 3M filters (reused)" filter bank used in a thermo-fogging filtration system in accordance with embodiments of the present disclosure. Chart 1400 includes a plot 1410, which illustrate a percentage of weight gain of each "two cheap and four 3M filters (reused)" filter of a filter bank (for example) used in an exemplary thermo-fogger filtration system having a total "fog" application time of 125 minutes.

Table 28 is a summary of the weight gain of the "two cheap and four 3M filters (reused)" filters tested (due to air-borne substances being captured by each filter, for example):

TABLE 28

| Filters Weight (g) | | | | |
|---|---|---|---|---|
| # | Before | After | Δ m | % W. Gain |
| 1 | 123.26 | 316.59 | 193.33 | 156.8 |
| 2 | 130.54 | 274.26 | 143.72 | 110.1 |
| 3 | 324.74 | 468.45 | 143.71 | 44.3 |
| 4 | 360.24 | 449.26 | 89.02 | 24.7 |
| 5 | 402.02 | 453.92 | 51.9 | 12.9 |
| 6 | 447.07 | 483.53 | 36.46 | 8.2 |
| Total | 1787.87 | 2446.01 | 658.14 | 36.8 |

Table 29 is a summary of an analysis of the aerosol reduction in a thermo-fogging filtration system using "two cheap and four 3M filters (reused)" filters tested:

TABLE 29

| Aerosol Analysis | | | | |
|---|---|---|---|---|
| Sampling Time (min) | Pre-Filter mg Pyr./M$^3$ | After-Filter mg Pyr./M$^3$ | AI Reduction (Times) | % Reduction |
| 5 | 940 | 510 | 1.8 | 45.7 |
| 35 | 2740 | 390 | 7.0 | 85.8 |
| 65 | 640 | 80 | 8.0 | 87.5 |
| 95 | 620 | 70 | 8.9 | 88.7 |
| 125 | 400 | 60 | 6.7 | 85.0 |

Figure 15:
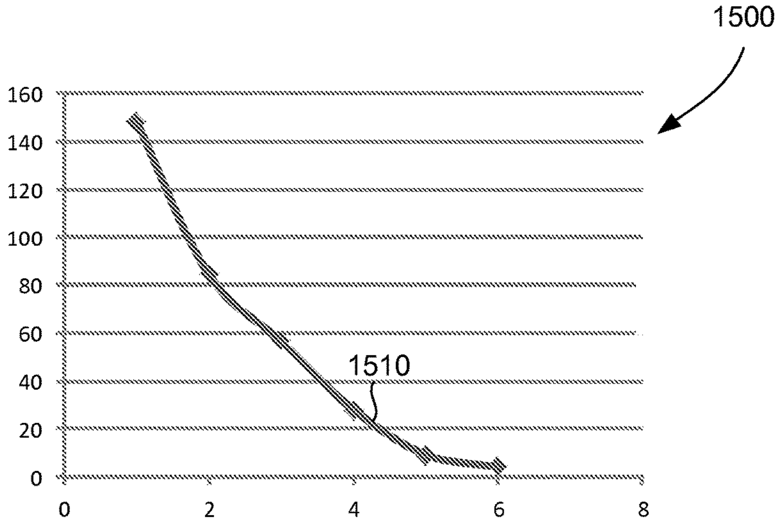
FIG. 15 is a plot diagram that illustrates the efficiency of a "20×25 3M filters (new)" filter bank used in a thermo-fogging filtration system in accordance with embodiments of the present disclosure.

FIG. 15 is a plot diagram that illustrates the efficiency of a “20×25 3M filters (new)” filter bank used in a thermo-fogging filtration system in accordance with embodiments of the present disclosure. Chart 1500 includes a plot 1510, which illustrate a percentage of weight gain of each “20×25 3M filters (new)” filter of a filter bank (for example) used in an exemplary thermo-fogger filtration system having a total “fog” application time of 125 minutes.

Table 30 is a summary of the weight gain of the “20×25 3M filters (new)” filters tested (due to air-borne substances being captured by each filter, for example):

TABLE 30

| Filters Weight (g) | | | | |
|---|---|---|---|---|
| # | Before | After | Δ m | % W. Gain |
| 1 | 302.25 | 751 | 448.75 | 148.5 |
| 2 | 301.82 | 556.5 | 254.68 | 84.4 |
| 3 | 339.90 | 532.35 | 192.54 | 56.6 |
| 4 | 301.25 | 385.84 | 84.59 | 28.1 |
| 5 | 303.84 | 332.1 | 28.26 | 9.3 |
| 6 | 302.92 | 315.63 | 12.71 | 4.2 |
| Total | 1851.98 | 2873.42 | 1021.44 | 55.2 |

Table 31 is a summary of an analysis of the aerosol reduction in a thermo-fogging filtration system using “20×25 3M filters (new)” filters tested:

TABLE 31

| Aerosol Analysis | | | | |
|---|---|---|---|---|
| Sampling Time (min) | Pre-Filter mg Pyr./M$^3$ | After-Filter mg Pyr./M$^3$ | AI Reduction (Times) | % Reduction |
| 5 | 960 | 50 | 19.2 | 94.8 |
| 35 | 2100 | 40 | 52.5 | 98.1 |
| 65 | 480 | 60 | 8.0 | 87.5 |
| 95 | 390 | 60 | 6.5 | 84.6 |
| 125 | 210 | 40 | 5.3 | 81.0 |

Figure 16:
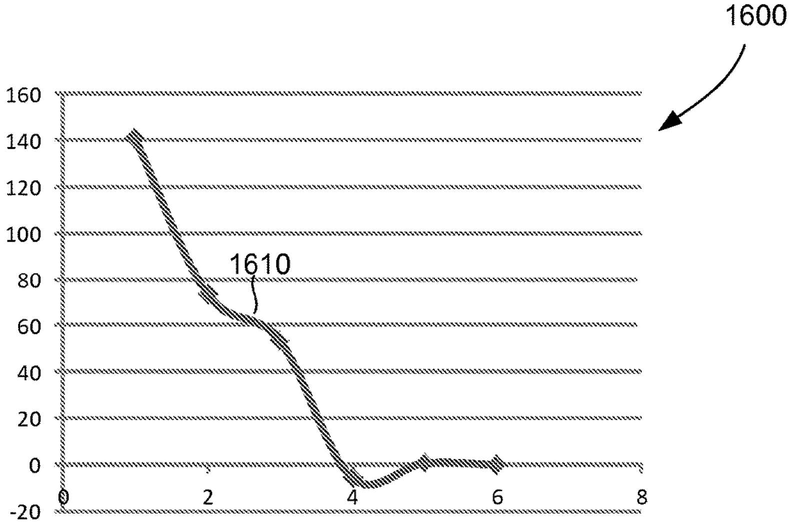
FIG. 16 is a plot diagram that illustrates the efficiency of a "20×25 3M filters (reused)" filter bank used in a thermo-fogging filtration system in accordance with embodiments of the present disclosure.

FIG. 16 is a plot diagram that illustrates the efficiency of a “20×25 3M filters (reused)” filter bank used in a thermo-fogging filtration system in accordance with embodiments of the present disclosure. Chart 1600 includes a plot 1610, which illustrate a percentage of weight gain of each “20×25 3M filters (reused)” filter of a filter bank (for example) used in an exemplary thermo-fogger filtration system having a total “fog” application time of 100 minutes.

Table 32 is a summary of the weight gain of the “20×25 3M filters (reused)” filters tested (due to air-borne substances being captured by each filter, for example):

TABLE 32

| Filters Weight (g) | | | | |
|---|---|---|---|---|
| # | Before | After | Δ m | % W. Gain |
| 1 | 315.63 | 759.3 | 443.67 | 140.6 |
| 2 | 332.1 | 575.72 | 243.62 | 73.4 |
| 3 | 385.84 | 592.72 | 206.88 | 53.6 |
| 4 | 532.35 | 501.64 | −30.71 | −5.8 |
| 5 | 556.5 | 559.66 | 3.16 | 0.6 |
| 6 | 751 | 750.17 | −0.83 | −0.1 |
| Total | 2873.42 | 3739.21 | 865.79 | 30.1 |

Table 33 is a summary of an analysis of the aerosol reduction in a thermo-fogging filtration system using “20×25 3M filters (reused)” filters tested:

TABLE 33

| Aerosol Analysis | | | | |
|---|---|---|---|---|
| Sampling Time (min) | Pre-Filter mg Pyr./M$^3$ | After-Filter mg Pyr./M$^3$ | AI Reduction (Times) | % Reduction |
| 5 | 500 | 70 | 7.1 | 86.0 |
| 35 | 2090 | 160 | 13.1 | 92.3 |
| 65 | 880 | 150 | 5.9 | 83.0 |
| 95 | 540 | 90 | 6.0 | 83.3 |

The efficiency of an “activated carbon (large granules) 20×20×6” filter used in a thermo-fogging filtration system in accordance with embodiments of the present disclosure is now discussed. Tables 34 and 35 illustrate measurements taken when using an “activated carbon (large granules) 20×20×6” filter (for example) used in an exemplary thermo-fogger filtration system having a total “fog” application time of 125 minutes.

Table 34 is a summary of the weight gain of the “activated carbon (large granules) 20×20×6” filters tested (due to air-borne substances being captured by each filter, for example):

TABLE 34

| Filters Weight (g) | | | | |
|---|---|---|---|---|
| # | Before | After | Δ m | % W. Gain |
| 1 | 17345.37 | 18198.1 | 852.8 | 4.9 |
| Total | 17345.4 | 18198.1 | 852.8 | 4.9 |

Table 35 is a summary of an analysis of the aerosol reduction in a thermo-fogging filtration system using “activated carbon (large granules) 20×20×6” filters tested:

TABLE 35

| Aerosol Analysis | | | | |
|---|---|---|---|---|
| Sampling Time (min) | Pre-Filter mg Pyr./M$^3$ | After-Filter mg Pyr./M$^3$ | AI Reduction (Times) | % Reduction |
| 5 | 910 | 880 | 1.0 | 3.3 |
| 35 | 2110 | 400 | 5.3 | 81.0 |
| 65 | 1370 | 240 | 5.7 | 82.5 |
| 95 | 430 | 240 | 1.8 | 44.2 |
| 125 | 160 | 90 | 1.8 | 43.8 |

The efficiency of an "activated carbon (large granules) 20×20×12" filter used in a thermo-fogging filtration system in accordance with embodiments of the present disclosure is now discussed. Tables 36 and 37 illustrate measurements taken when using an "activated carbon (large granules) 20×20×12" filter (for example) used in an exemplary thermo-fogger filtration system having a total "fog" application time of 205 minutes.

Table 36 is a summary of the weight gain of the "activated carbon (large granules) 20×20×12" filters tested (due to air-borne substances being captured by each filter, for example):

TABLE 36

| Filters Weight (g) | | | | |
|---|---|---|---|---|
| # | Before | After | Δ m | % W. Gain |
| 1 | 55905.26 | 56744.4 | 839.1 | 1.5 |
| Total | 55905.3 | 56744.4 | 839.1 | 1.5 |

Table 37 is a summary of an analysis of the aerosol reduction in a thermo-fogging filtration system using "activated carbon (large granules) 20×20×12" filters tested:

TABLE 37

| Aerosol Analysis | | | | |
|---|---|---|---|---|
| Sampling Time (min) | Pre-Filter mg Pyr./$M^3$ | After-Filter mg Pyr./$M^3$ | AI Reduction (Times) | % Reduction |
| 5 | 1080 | 780 | 1.4 | 27.8 |
| 45 | 520 | 460 | 1.1 | 11.5 |
| 85 | 320 | 190 | 1.7 | 40.6 |
| 125 | 130 | 120 | 1.1 | 7.7 |
| 165 | 110 | 100 | 1.1 | 9.1 |
| 205 | 60 | 60 | 1.0 | 0.0 |

Figure 17:
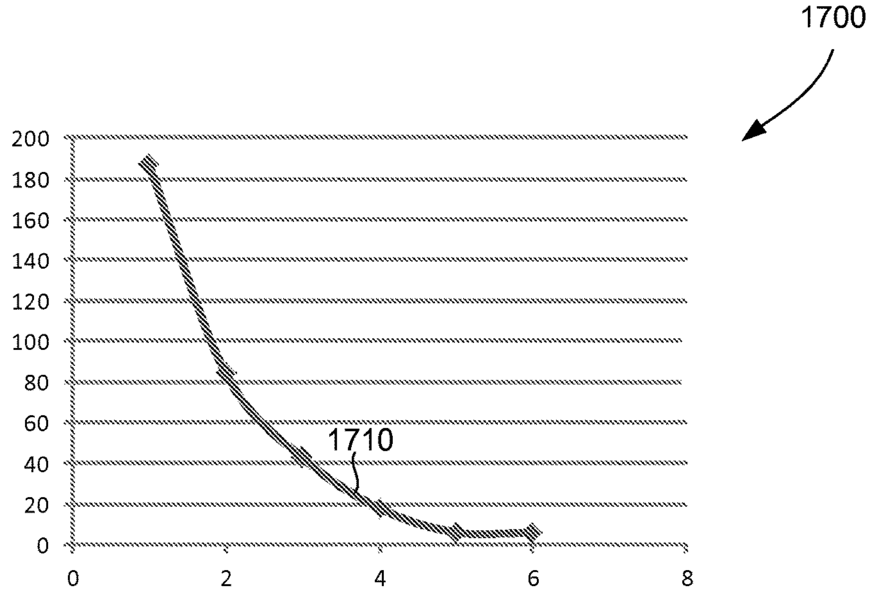
FIG. 17 is a plot diagram that illustrates the efficiency of a "20×25 3M filters (1900 EcoFOG)" filter bank used in a thermo-fogging filtration system in accordance with embodiments of the present disclosure.

FIG. 17 is a plot diagram that illustrates the efficiency of a "20×25 3M filters (1900 EcoFOG 100)" filter bank used in a thermo-fogging filtration system in accordance with embodiments of the present disclosure. "EcoFOG 100" contains diphenylamine as the active ingredient and is available from Pace International, LLC. Chart 1700 includes a plot 1710, which illustrate a percentage of weight gain of each "20×25 3M filters (1900 EcoFOG 100)" filter of a filter bank (for example) used in an exemplary thermo-fogger filtration system having a total "fog" application time of 125 minutes.

Table 38 is a summary of the weight gain of the "20×25 3M filters (1900 EcoFOG 100)" filters tested (due to air-borne substances being captured by each filter, for example):

TABLE 38

| Filters Weight (g) | | | | |
|---|---|---|---|---|
| # | Before | After | Δ m | % W. Gain |
| 1 | 338.35 | 971.6 | 633.25 | 187.2 |
| 2 | 313.66 | 577.78 | 264.12 | 84.2 |
| 3 | 311.55 | 444.85 | 133.3 | 42.8 |
| 4 | 311.76 | 367.11 | 55.35 | 17.8 |
| 5 | 298.76 | 316.28 | 17.52 | 5.9 |
| 6 | 302.62 | 320.26 | 17.64 | 5.8 |
| Total | 1876.7 | 2997.88 | 1121.18 | 59.7 |

Table 39 is a summary of an analysis of the aerosol reduction in a thermo-fogging filtration system using "20×25 3M filters (1900 EcoFOG 100)" filters tested:

TABLE 39

| Aerosol Analysis | | | | |
|---|---|---|---|---|
| Sampling Time (min) | Pre-Filter mg DPA/$M^3$ | After-Filter mg DPA/$M^3$ | AI Reduction (Times) | % Reduction |
| 5 | 734.40 | 0 | 734.0 | 100.0 |
| 35 | 3369.0 | 21.8 | 154.9 | 99.4 |
| 65 | 938.0 | 5.0 | 188.0 | 99.5 |
| 95 | 173.5 | 4.4 | 39.0 | 97.4 |
| 125 | 125.3 | 0.0 | 125.3 | 100.0 |
| 155 | 24.31 | 8.8 | 2.7 | 63.6 |

Figure 18:
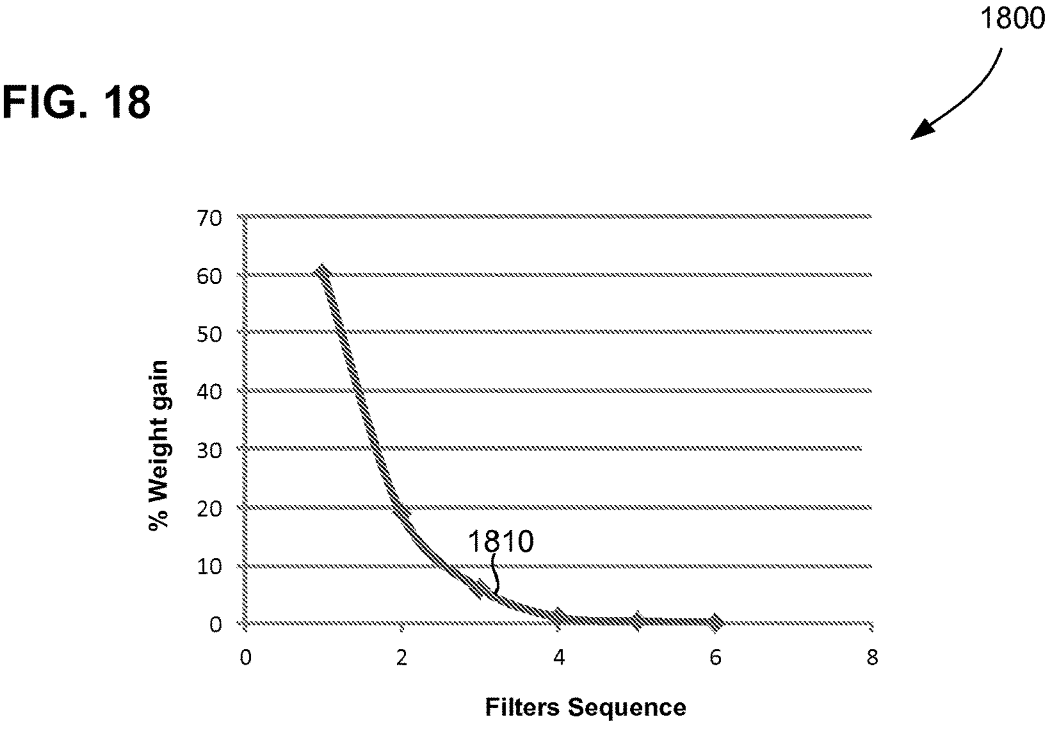
FIG. 18 is a plot diagram that illustrates the efficiency of a "20×25 3M filters (1900 Melted DPA)" filter bank used in a thermo-fogging filtration system in accordance with embodiments of the present disclosure.

FIG. 18 is a plot diagram that illustrates the efficiency of a "20×25 3M filters (1900 Melted DPA)" filter bank used in a thermo-fogging filtration system in accordance with embodiments of the present disclosure. Chart 1800 includes a plot 1810, which illustrate a percentage of weight gain of each "20×25 3M filters (1900 Melted DPA)" filter of a filter bank (for example) used in an exemplary thermo-fogger filtration system having a total "fog" application time of 125 minutes.

Table 40 is a summary of the weight gain of the "20×25 3M filters (1900 Melted DPA)" filters tested (due to air-borne substances being captured by each filter, for example):

TABLE 40

| Filters Weight (g) | | | | |
|---|---|---|---|---|
| # | Before | After | Δ m | % W. Gain |
| 1 | 308.43 | 494.29 | 185.86 | 60.3 |
| 2 | 307.78 | 365.9 | 58.12 | 18.9 |
| 3 | 303.5 | 321.56 | 18.06 | 6.0 |
| 4 | 305.73 | 308.84 | 3.11 | 1.0 |
| 5 | 308.2 | 308.98 | 0.78 | 0.3 |
| 6 | 307.2 | 307.61 | 0.41 | 0.1 |
| Total | 1840.84 | 2107.18 | 266.34 | 14.5 |

Table 41 is a summary of an analysis of the aerosol reduction in a thermo-fogging filtration system using "20×25 3M filters (1900 Melted DPA)" filters tested:

TABLE 41

| Aerosol Analysis | | | | |
|---|---|---|---|---|
| Sampling Time (min) | Pre-Filter mg DPA/$M^3$ | After-Filter mg DPA/$M^3$ | AI Reduction (Times) | % Reduction |
| 5 | 850 | 1.85 | 459.5 | 99.8 |
| 35 | 3740 | 10 | 374.0 | 99.7 |
| 65 | 3120 | 7.74 | 403.1 | 99.8 |
| 95 | 1950 | 0.1 | 19500.0 | 100.0 |
| 125 | 760 | 0.1 | 7600.0 | 100.0 |

Figure 19:
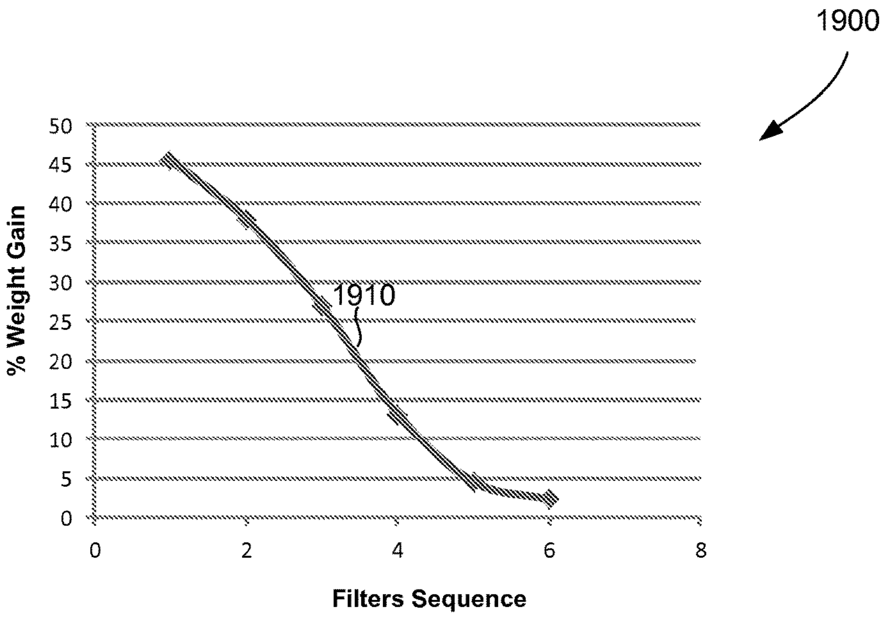
FIG. 19 is a plot diagram that illustrates the efficiency of a "20×25 3M filters (1900 new EcoFOG 100)" filter bank used in a thermo-fogging filtration system in accordance with embodiments of the present disclosure.

FIG. 19 is a plot diagram that illustrates the efficiency of a "20×25 3M filters (1900 new EcoFOG 100)" filter bank used in a thermo-fogging filtration system in accordance with embodiments of the present disclosure. Chart 1900 includes a plot 1910, which illustrate a percentage of weight gain of each "20×25 3M filters (1900 new EcoFOG 100)" filter of a filter bank (for example) used in an exemplary thermo-fogger filtration system having a total "fog" application time of 119 minutes.

Table 42 is a summary of the weight gain of the "20×25 3M filters (1900 new EcoFOG 100)" filters tested (due to substances being captured by each filter, for example):

TABLE 42

| Filters Weight (g) | | | | |
|---|---|---|---|---|
| # | Before | After | Δ m | % W. Gain |
| 1 | 306.6 | 446.2 | 139.6 | 45.5 |
| 2 | 306.1 | 422.4 | 116.3 | 38.0 |
| 3 | 304 | 386.1 | 82.1 | 27.0 |
| 4 | 306.2 | 346.5 | 40.3 | 13.2 |
| 5 | 304.4 | 318.1 | 13.7 | 4.5 |
| 6 | 305 | 3100 | 5 | 4.6 |
| Total | 1832.3 | 2229.3 | 397 | 21.7 |

Table 43 is a summary of an analysis of the aerosol reduction in a thermo-fogging filtration system using "20×25 3M filters (1900 new EcoFOG 100)" filters tested:

TABLE 43

| Aerosol Analysis | | | | |
|---|---|---|---|---|
| Sampling Time (min) | Pre-Filter mg DPA/M$^3$ | After-Filter mg DPA/M$^3$ | AI Reduction (Times) | % Reduction |
| 5 | 531.0 | 175.0 | 3.0 | 67.0 |
| 30 | 935.0 | 128.0 | 7.3 | 86.3 |
| 60 | 1023.0 | 138.0 | 7.4 | 86.5 |
| 90 | 903.0 | 139.0 | 6.5 | 84.6 |
| 119 | 946.0 | 137.0 | 6.9 | 85.5 |

Figure 20:
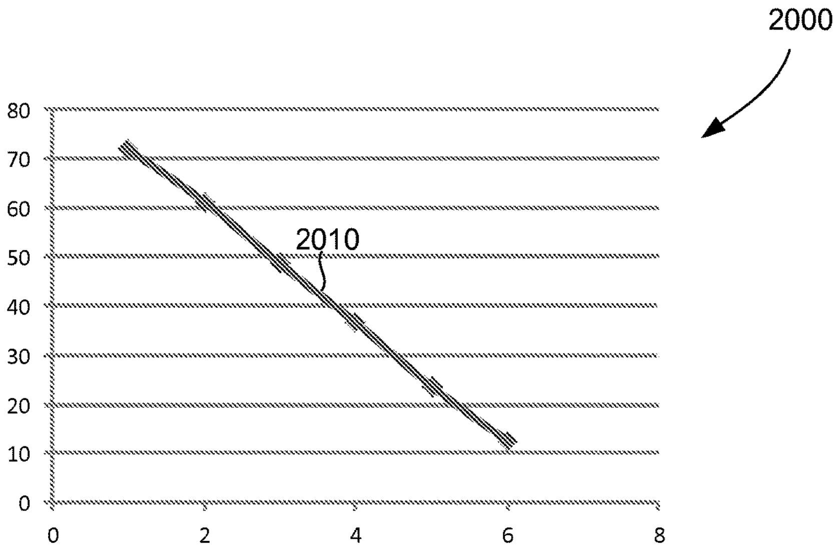
FIG. 20 is a plot diagram that illustrates the efficiency of a "20×25 3M filters (1900 new EcoFOG 100)" filter bank used in a thermo-fogging filtration system in accordance with embodiments of the present disclosure.

FIG. 20 is a plot diagram that illustrates the efficiency of a "20×25 3M filters (1900 new EcoFOG 100)" filter bank used in a thermo-fogging filtration system in accordance with embodiments of the present disclosure. Chart 2000 includes a plot 2010, which illustrate a percentage of weight gain of each "20×25 3M filters (1900 new EcoFOG 100)" filter of a filter bank (for example) used in an exemplary thermo-fogger filtration system having a total "fog" application time of 65 minutes in a first room and 80 in a second room.

Table 44 is a summary of the weight gain of the "20×25 3M filters (1900 new EcoFOG 100)" filters after being used for filtering both rooms (sequentially):

TABLE 44

| Filters Weight (g) | | | | |
|---|---|---|---|---|
| # | Before | After | Δ m | % W. Gain |
| 1 | 308.58 | 530 | 221.42 | 71.8 |
| 2 | 309.97 | 499.6 | 189.63 | 61.2 |
| 3 | 309.74 | 460.1 | 150.36 | 48.5 |
| 4 | 310.56 | 424.4 | 113.84 | 36.7 |
| 5 | 307.53 | 380.3 | 72.77 | 23.7 |
| 6 | 309.12 | 347.7 | 38.58 | 12.5 |
| Total | 1855.5 | 2642.1 | 786.6 | 42.4 |

Table 45 is a summary of an analysis of the aerosol reduction in a thermo-fogging filtration system using "20×25 3M filters (1900 new EcoFOG 100)" filters tested in the first room:

TABLE 45

| Aerosol Analysis | | | | |
|---|---|---|---|---|
| Sampling Time (min) | Pre-Filter mg Pyr./M$^3$ | After-Filter mg Pyr./M$^3$ | AI Reduction (Times) | % Reduction |
| 5 | 351.0 | 33.0 | 10.5 | 90.6 |
| 20 | 830.0 | 6.0 | 138.3 | 99.3 |
| 35 | 517.0 | 3.0 | 172.3 | 99.4 |
| 50 | 868.0 | 6.0 | 1447 | 99.3 |
| 65 | 534.0 | 17.0 | 31.4 | 96.8 |

Table 46 is a summary of an analysis of the aerosol reduction in a thermo-fogging filtration system using "20×25 3M filters (1900 new EcoFOG 160)" filters tested in the second room:

TABLE 46

| Aerosol Analysis | | | | |
|---|---|---|---|---|
| Sampling Time (min) | Pre-Filter mg Pyr./M$^3$ | After-Filter mg Pyr./M$^3$ | AI Reduction (Times) | % Reduction |
| 5 | 249.0 | 5.0 | 49.8 | 98.0 |
| 20 | 1188.0 | 14.0 | 84.9 | 98.8 |
| 35 | 731.0 | 53.0 | 13.8 | 92.7 |
| 50 | 1108.0 | 38.0 | 29.2 | 96.6 |
| 65 | 949.0 | 50.0 | 19.0 | 94.7 |
| 80 | 858.0 | 276.0 | 3.1 | 67.8 |

Figure 21:
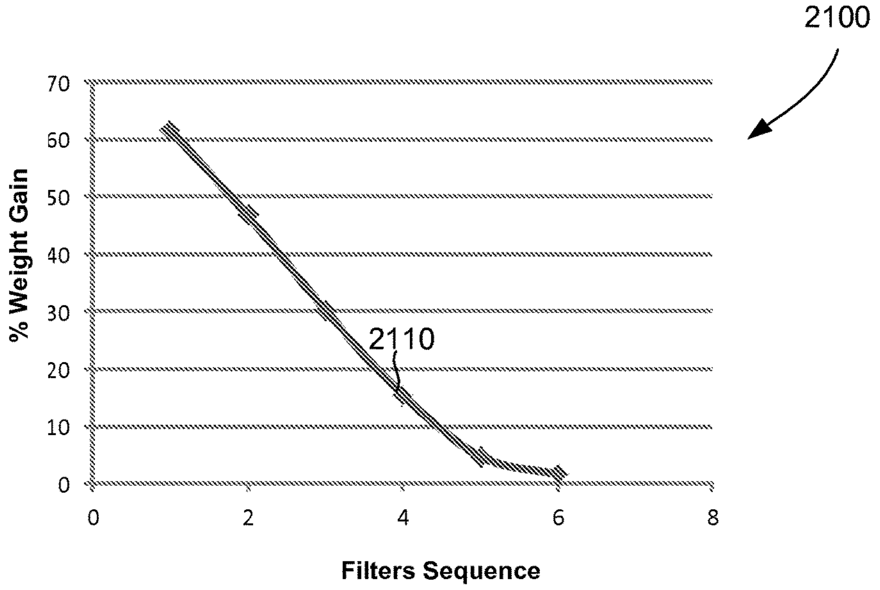
FIG. 21 is a plot diagram that illustrates the efficiency of a "six new 3M filters (EcoFOG 160)" filter bank used in a thermo-fogging filtration system in accordance with embodiments of the present disclosure.

FIG. 21 is a plot diagram that illustrates the efficiency of a "six new 3M filters (EcoFOG 160)" filter bank used in a thermo-fogging filtration system in accordance with embodiments of the present disclosure. "EcoFOG 160" contains pyrimethanil as the active ingredient and is available from Pace International, LLC. Chart 2100 includes a plot 2110, which illustrate a percentage of weight gain of each "six new 3M filters (EcoFOG 160)" filter of a filter bank (for example) used in an exemplary thermo-fogger filtration system having a total "fog" application time of 118 minutes.

Table 47 is a summary of the weight gain of the "six new 3M filters (EcoFOG 160)" filters tested (due to substances being captured by each filter, for example):

TABLE 47

| Filters Weight (g) | | | | |
|---|---|---|---|---|
| # | Before | After | Δ m | % W. Gain |
| 1 | 310.6 | 501.8 | 191.2 | 61.6 |
| 2 | 308.8 | 452.9 | 144.1 | 46.7 |
| 3 | 309.8 | 403.4 | 93.6 | 30.2 |
| 4 | 311.6 | 359.8 | 48.2 | 15.5 |
| 5 | 308.7 | 323.3 | 14.6 | 4.7 |
| 6 | 309.1 | 313.9 | 4.8 | 1.6 |
| Total | 1858.6 | 2355.1 | 496.5 | 26.7 |

Table 48 is a summary of an analysis of the aerosol reduction in a thermo-fogging filtration system using "six new 3M filters (EcoFOG 160)" filters tested:

TABLE 48

| Aerosol Analysis | | | | |
|---|---|---|---|---|
| Sampling Time (min) | Pre-Filter mg Pyr./$M^3$ | After-Filter mg Pyr./$M^3$ | AI Reduction (Times) | % Reduction |
| 6 | 413.0 | 1.0 | 413.0 | 99.8 |
| 60 | 289.0 | 2.0 | 144.5 | 99.3 |
| 118 | 4734.0 | 9.0 | 526.0 | 99.8 |

Figure 22:
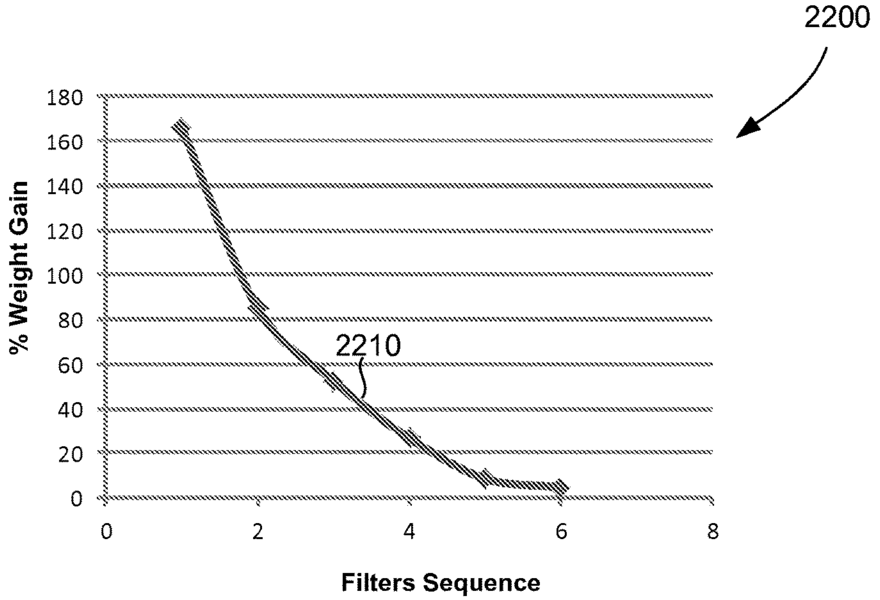
FIG. 22 is a plot diagram that illustrates the efficiency of a "20×25 3M filters (2200 plus two inches of activated carbon EcoFOG 160 2L)" filter bank used in a thermo-fogging filtration system in accordance with embodiments of the present disclosure.

FIG. 22 is a plot diagram that illustrates the efficiency of a "20×25 3M filters (2200 plus two inches of activated carbon EcoFOG 160 2L)" filter bank used in a thermo-fogging filtration system in accordance with embodiments of the present disclosure. Chart 2200 includes a plot 2210, which illustrate a percentage of weight gain of each "20×25 3M filters (2200 plus two inches of activated carbon EcoFOG 160 2L)" filter of a filter bank (for example) used in an exemplary thermo-fogger filtration system having a total "fog" application time of 125 minutes.

Table 49 is a summary of the weight gain of the "20×25 3M filters (2200 plus two inches of activated carbon EcoFOG 160 2L)" filters tested:

TABLE 49

| Filters Weight (g) | | | | |
|---|---|---|---|---|
| # | Before | After | Δ m | % W. Gain |
| 1 | 313.04 | 833.24 | 520.2 | 166.2 |
| 2 | 312 | 577.42 | 265.42 | 85.1 |
| 3 | 312.8 | 477.33 | 164.53 | 52.6 |
| 4 | 310.76 | 393.93 | 83.17 | 26.8 |
| 5 | 312.25 | 388.6 | 26.35 | 8.4 |
| 6 | 314.65 | 328.98 | 14.33 | 4.6 |
| Total | 1875.5 | 2949.5 | 1074 | 57.3 |

Figure 23:
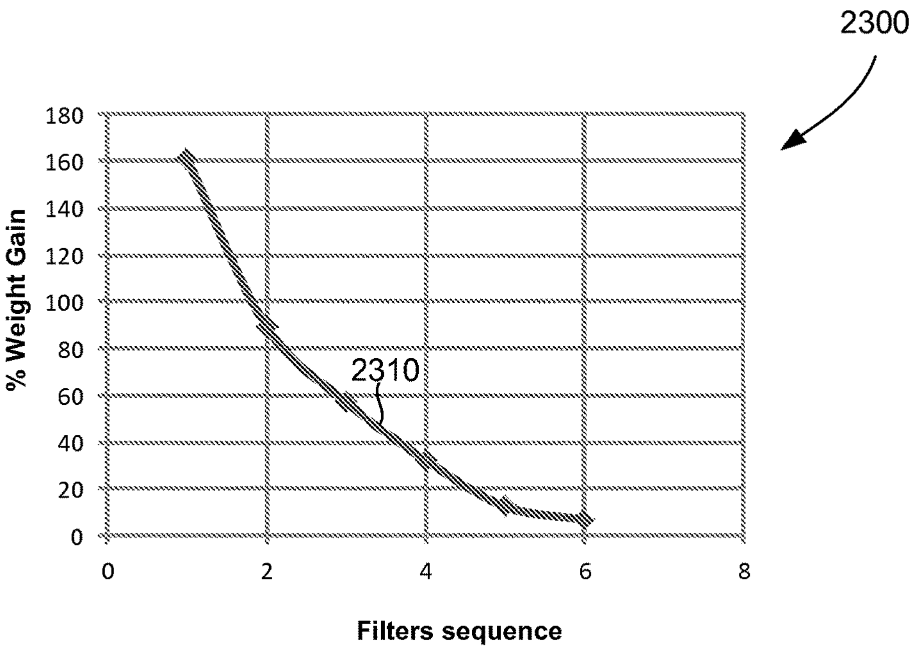
FIG. 23 is a plot diagram that illustrates the efficiency in a second test of a "20×25 3M filters (2200 plus two inches of activated carbon EcoFOG 160 2L)" filter bank used in a thermo-fogging filtration system in accordance with embodiments of the present disclosure.

FIG. 23 is a plot diagram that illustrates the efficiency in a second test of a "20×25 3M filters (2200 plus two inches of activated carbon EcoFOG 160 2L)" filter bank used in a thermo-fogging filtration system in accordance with embodiments of the present disclosure. Chart 2300 includes a plot 2310, which illustrate a percentage of weight gain of each "20×25 3M filters (2200 plus two inches of activated carbon EcoFOG 160 2L)" filter of a filter bank (for example) used in an exemplary thermo-fogger filtration system having a total "fog" application time of 125 minutes.

Table 50 is a summary of the weight gain of the "20×25 3M filters (2200 plus two inches of activated carbon EcoFOG 160 2L)" filters tested (due to substances being captured by each filter, for example):

TABLE 50

| Filters Weight (g) | | | | |
|---|---|---|---|---|
| # | Before | After | Δ m | % W. Gain |
| 1 | 312.98 | 817.35 | 504.37 | 161.2 |
| 2 | 312.36 | 591.01 | 278.65 | 89.2 |
| 3 | 310.89 | 488.75 | 177.86 | 57.2 |
| 4 | 311.74 | 411.82 | 100.08 | 32.1 |
| 5 | 313.38 | 352.06 | 38.68 | 12.3 |
| 6 | 313.24 | 334.61 | 21.37 | 6.8 |
| Total | 1874.59 | 2995.6 | 1121.01 | 59.8 |

Table 51 is a summary of an analysis of the aerosol reduction in a thermo-fogging filtration system using "20×25 3M filters (2200 plus two inches of activated carbon EcoFOG 160 2L)" filters tested:

TABLE 51

| Aerosol Analysis | | | | | | |
|---|---|---|---|---|---|---|
| Sampling Time (min) | Pre-Filter EtOAC Relative Concentration (No m.u.) | After-Fiber Filter EtOAC Relative Concentration (No m.u.) | After-Carbon Filter EtOAC Relative Concentration (No m.u.) | % Reduction Fiber | % Reduction Carbon | % Reduction Total |
| 35 | 567607 | 407245 | 38926 | 28.252294 | 90.44163 | 93.14209 |
| 65 | 235369 | 235103 | 30088 | 0.113014 | 87.2022 | 87.21667 |
| 95 | 169475 | 170857 | 68086 | −0.81546 | 60.1503 | 59.82534 |
| 125 | 144186 | 371199 | 35583 | −157.4446 | 90.41404 | 75.32146 |

The parts per million (ppm) values presented in Tables 52-56 below are the concentrations of diphenylamine detected in samples collected immediately before the filters (Pre-filter) and immediately after the filters (After-Filter).

Table 52 is a summary of the weight gain of the six "20×25 3M filters (1900 EcoFOG 170)" filters tested (due to air-borne substances being captured by each filter, for example) under 40 CFM. "EcoFOG 170" contains diphenylamine as the active ingredient and is available from Pace International, LLC.

TABLE 52

| Aerosol Analysis | | | |
|---|---|---|---|
| Sampling Time (min) | Pre-Filter DPA ppm | After-Filter DPA ppm | % Reduction |
| 5 | 57.13 | 0.10 | 99.8 |
| 35 | 157.74 | 0.10 | 99.9 |
| 65 | 77.18 | 0.00 | 100.0 |
| 95 | 19.96 | 0.00 | 100.0 |
| 125 | 11.90 | 0.00 | 100.0 |

Table 53 is a summary of the weight gain of the seven "20×25 3M filters (1900 EcoFOG 170)" filters tested (due to air-borne substances being captured by each filter, for example) under 40 CFM:

TABLE 53

| Aerosol Analysis | | | |
|---|---|---|---|
| Sampling Time (min) | Pre-Filter DPA ppm | After-Filter DPA ppm | % Reduction |
| 5 | 62.39 | 2.15 | 96.6 |
| 35 | 152.30 | 0.10 | 99.9 |

TABLE 53-continued

| Aerosol Analysis | | | |
|---|---|---|---|
| Sampling Time (min) | Pre-Filter DPA ppm | After-Filter DPA ppm | % Reduction |
| 65 | 38.00 | 0.00 | 100.0 |
| 95 | 8.15 | 0.00 | 100.0 |
| 125 | 21.82 | 0.00 | 100.0 |

Table 54 is a summary of the weight gain of the eight "20×25 3M filters (1900 EcoFOG 170)" filters tested (due to air-borne substances being captured by each filter, for example) under 40 CFM:

TABLE 54

| Aerosol Analysis | | | |
|---|---|---|---|
| Sampling Time (min) | Pre-Filter DPA ppm | After-Filter DPA ppm | % Reduction |
| 5 | 114.55 | 2.12 | 98.1 |
| 35 | 71.12 | 0.10 | 99.9 |
| 65 | 43.05 | 0.00 | 100.0 |
| 95 | 7.83 | 0.00 | 100.0 |
| 125 | 18.45 | 0.00 | 100.0 |

Table 55 is a summary of the weight gain of the six "20×25 3M filters (1900 EcoFOG 170)" filters tested (due to air-borne substances being captured by each filter, for example) under 40 CFM and −0.25 IWC:

TABLE 55

| Aerosol Analysis | | | |
|---|---|---|---|
| Sampling Time (min) | Pre-Filter DPA ppm | After-Filter DPA ppm | % Reduction |
| 5 | 166.79 | 11.40 | 93.2 |
| 35 | 149.01 | 1.06 | 99.3 |
| 65 | 25.13 | 6.28 | 75.0 |
| 95 | 2.96 | 0.00 | 100.0 |
| 125 | 2.01 | 0.00 | 100.0 |

Table 56 is a summary of the weight gain of the six "20×25 3M filters (1900 EcoFOG 170)" filters tested (due to air-borne substances being captured by each filter, for example) under 80 CFM:

TABLE 56

| Aerosol Analysis | | | |
|---|---|---|---|
| Sampling Time (min) | Pre-Filter DPA ppm | After-Filter DPA ppm | % Reduction |
| 5 | 181.31 | 7.58 | 95.8 |
| 35 | 82.00 | 0.10 | 99.9 |
| 65 | 40.00 | 0.00 | 100.0 |
| 95 | 14.00 | 0.00 | 100.0 |
| 125 | 5.36 | 0.10 | 98.1 |

The results of the tests in Tables 52-54 demonstrate that increases in the number of filters from six filters to eight filters resulted in substantially the same effectiveness.

The results of the tests in Tables 52 and 55 demonstrate that reducing the room pressure from −0.15-0 inch WC to −0.25 inch WC resulted in substantially the same performance.

The results of the tests in Tables 52 and 56 demonstrated that increasing the air flow from 40 CFM to 80 CFM resulted in substantially the same performance.

The parts per million (ppm) values presented in Tables 57-66 below are the concentrations of thiabendazole ("TBZ") or fludioxonil ("FDL") detected in samples collected immediately before the filters (Pre-filter) and immediately after the filters (After-Filter).

Table 57 is a summary of the weight gain of the six "20×25 3M filters (1900 EcoFOG 99)" filters tested (due to air-borne substances being captured by each filter, for example) under 40 CFM. "EcoFOG 99" contains thiabendazole as the active ingredient and is available from Pace International, LLC.

TABLE 57

| AEROSOL ANALYSIS | | | |
|---|---|---|---|
| Sampling Time (min.) | Pre-Filter TBZ ppm | After-Filter TBZ ppm | % Reduction |
| 5 | 31.85 | 0.00 | 100.0 |
| 35 | 51.03 | 0.34 | 99.3 |
| 65 | 23.38 | 0.00 | 100.0 |
| 95 | 12.45 | 0.00 | 100.0 |
| 125 | 5.72 | 0.00 | 100.0 |

Table 58 is a summary of the weight gain of the seven "20×25 3M filters (1900 EcoFOG 99)" filters tested (due to air-borne substances being captured by each filter, for example) under 40 CFM:

TABLE 58

| AEROSOL ANALYSIS | | | |
|---|---|---|---|
| Sampling Time (min.) | Pre-Filter ppm | After-Filter ppm | % Reduction |
| 5 | 132.80 | 0.01 | 100.0 |
| 35 | 46.35 | 0.01 | 100.0 |
| 65 | 13.19 | 0.01 | 99.9 |
| 95 | 6.32 | 0.01 | 99.8 |
| 125 | 4.30 | 0.01 | 99.8 |

Table 59 is a summary of the weight gain of the eight "20×25 3M filters (1900 EcoFOG 99)" filters tested (due to air-borne substances being captured by each filter, for example) under 40 CFM:

TABLE 59

| AEROSOL ANALYSIS | | | |
|---|---|---|---|
| Sampling Time (min.) | Pre-Filter TBZ ppm | After-Filter TBZ ppm | % Reduction |
| 5 | 91.50 | 0.01 | 100.0 |
| 35 | 49.08 | 3.57 | 92.7 |
| 65 | 38.05 | 0.95 | 97.5 |
| 95 | 16.33 | 1.06 | 93.5 |
| 125 | 3.79 | 0.46 | 87.9 |

Table 60 is a summary of the weight gain of the six "20×25 3M filters (1900 EcoFOG 99)" filters tested (due to air-borne substances being captured by each filter, for example) under 40 CFM and −025 inches WC:

TABLE 60

| AEROSOL ANALYSIS | | | |
|---|---|---|---|
| Sampling Time (min.) | Pre-Filter TBZ ppm | After-Filter TBZ ppm | % Reduction |
| 5 | 57.58 | 1.15 | 98.0 |
| 35 | 69.75 | 0.50 | 99.3 |
| 65 | 10.26 | 0.44 | 95.7 |
| 95 | 6.08 | 0.01 | 99.8 |
| 125 | 7.56 | 0.26 | 96.6 |

Table 61 is a summary of the weight gain of the six "20×25 3M filters (1900 EcoFOG 99)" filters tested (due to air-borne substances being captured by each filter, for example) under 80 CFM:

TABLE 61

| AEROSOL ANALYSIS | | | |
|---|---|---|---|
| Sampling Time (min.) | Pre-Filter TBZ ppm | After-Filter TBZ ppm | % Reduction |
| 5 | 77.18 | 0.01 | 100.0 |
| 35 | 68.00 | 0.50 | 99.3 |
| 65 | 22.20 | 0.35 | 98.4 |
| 95 | 9.25 | 0.01 | 99.9 |
| 125 | 10.50 | 0.01 | 99.9 |

Table 62 is a summary of the weight gain of the six "20×25 3M filters (1900 EcoFOG 80)" filters tested (due to air-borne substances being captured by each filter, for example) under 40 CFM. "EcoFOG 80" contains fludioxonil as the active ingredient and is available from Pace International, LLC.

TABLE 62

| AEROSOL ANALYSIS | | | |
|---|---|---|---|
| Sampling Time (min.) | Pre-Filter FDL ppm | After-Filter FDL ppm | % Reduction |
| 5 | 19.36 | 2.53 | 86.9 |
| 35 | 47.24 | 0.00 | 100.0 |
| 65 | 22.28 | 0.00 | 100.0 |
| 95 | 6.48 | 0.00 | 100.0 |
| 125 | 3.82 | 0.00 | 100.0 |

Table 63 is a summary of the weight gain of the seven "20×25 3M filters (1900 EcoFOG 80)" filters tested (due to air-borne substances being captured by each filter, for example) under 40 CFM:

TABLE 63

| AEROSOL ANALYSIS | | | |
|---|---|---|---|
| Sampling Time (min.) | Pre-Filter FDL ppm | After-Filter FDL ppm | % Reduction |
| 5 | 49.70 | 0.00 | 100.0 |
| 35 | 38.32 | 0.00 | 100.0 |
| 65 | 28.20 | 0.00 | 100.0 |
| 95 | 7.46 | 0.00 | 100.0 |
| 125 | 5.30 | 0.00 | 100.0 |

Table 64 is a summary of the weight gain of the eight "20×25 3M filters (1900 EcoFOG 80)" filters tested (due to air-borne substances being captured by each filter, for example) under 40 CFM:

TABLE 64

| AEROSOL ANALYSIS | | | |
|---|---|---|---|
| Sampling Time (min.) | Pre-Filter FDL ppm | After-Filter FDL ppm | % Reduction |
| 5 | 29.90 | 0.00 | 100.0 |
| 35 | 38.04 | 0.00 | 100.0 |
| 65 | 14.96 | 0.00 | 100.0 |
| 95 | 7.75 | 0.00 | 100.0 |
| 125 | 4.24 | 0.00 | 100.0 |

Table 65 is a summary of the weight gain of the six "20×25 3M filters (1900 EcoFOG 80)" filters tested (due to air-borne substances being captured by each filter, for example) under 40 CFM and −0.25 inches WC:

TABLE 65

| AEROSOL ANALYSIS | | | |
|---|---|---|---|
| Sampling Time (min.) | Pre-Filter FDL ppm | After-Filter FDL ppm | % Reduction |
| 5 | 32.37 | 0.00 | 100.0 |
| 35 | 73.44 | 0.00 | 100.0 |
| 65 | 9.68 | 0.00 | 100.0 |
| 95 | 3.15 | 0.00 | 100.0 |
| 125 | 4.88 | 0.00 | 100.0 |

Table 66 is a summary of the weight gain of the six "20×25 3M filters (1900 EcoFOG 80)" filters tested (due to air-borne substances being captured by each filter, for example) under 80 CFM:

TABLE 66

| AEROSOL ANALYSIS | | | |
|---|---|---|---|
| Sampling Time (min.) | Pre-Filter FDL ppm | After-Filter FDL ppm | % Reduction |
| 5 | 82.09 | 0.00 | 100.0 |
| 35 | 41.83 | 0.00 | 100.0 |
| 65 | 20.79 | 0.00 | 100.0 |
| 95 | 0.00 | 0.00 | #DIV/0! |
| 125 | 0.00 | 0.00 | #DIV/0! |

The results of the tests in Tables 57-66 demonstrate that when the number of filters is at least six, the present invention is effective utilizing fludioxonil and thiabendazole as the post-harvest treatment chemical.

The results of the tests in Tables 57-66 demonstrate that when the pressure is between −0.25 and 0 inches pressure in the water column, the present invention is effective utilizing TBZ and FDL as the post-harvest treatment chemical.

The results of the tests in Tables 57-66 demonstrate that at air flow rates up to 80 CFM, the present invention is effective utilizing TBZ and FDL as the post-harvest treatment chemical.

The various exemplary embodiments described above are provided by way of illustration only and should not be construed to limit the claims attached hereto. Those skilled in the art will readily recognize various modifications and changes that could be made without following the example exemplary embodiments and applications illustrated and described herein, and without departing from the true spirit and scope of the following claims.

What is claimed is:

1. A method for filtration, comprising: arranging fruits in a substantially closed room having a volume of air; introducing post-harvest chemicals selected from the group consisting of thiabendazole, fludioxonil and a mixture thereof, and optionally, additional treatment substances, into an airstream with a thermo-fogger gun to generate air-borne treatment substances at a rate of up to 80 cubic feet per minute;

introducing the airstream and the air-borne treatment substances into the volume of air of the substantially closed room to generate the dispersed air-borne substances;

creating with a fan a pressure between −0.25 and 0 inches water column upon a bank of at least six high particle-rated pleated fiber filters; and inducing an exhaust air current that flows from the substantially closed room into an exhaust port of the substantially closed room, wherein the exhaust air current includes the air-borne substances from the exhaust port and the filter bank captures at least around 95 percent of the air-borne treatment substances.

2. The method of claim 1, wherein ambient air is used as input to the thermo-fogger gun.

3. A method for filtration, comprising: arranging vegetables in a substantially closed room having a volume of air; introducing post-harvest chemicals selected from the group consisting of thiabendazole, fludioxonil and a mixture thereof, and optionally, additional treatment substances, into an airstream with a thermo-fogger gun to generate air-borne treatment substances at a rate of up to 80 cubic feet per minute;

introducing the airstream and the air-borne treatment substances into the volume of air of the substantially closed room to generate the dispersed air-borne substances;

creating with a fan a pressure between −0.25 and 0 inches water column upon a bank of at least six high particle-rated pleated fiber filters; and inducing an exhaust air current that flows from the substantially closed room into an exhaust port of the substantially closed room, wherein the exhaust air current includes the air-borne substances from the exhaust port and the filter bank captures at least around 95 percent of the air-borne treatment substances.

4. The method of claim 3, wherein ambient air is used as input to the thermo-fogger gun.

* * * * *